United States Patent
Dean et al.

(10) Patent No.: US 6,962,674 B2
(45) Date of Patent: Nov. 8, 2005

(54) DISSOLUTION TEST APPARATUS

(75) Inventors: Stephen D. Dean, Cary, NC (US);
James E. Swon, Chapel Hill, NC (US);
C. J. Anthony Fernando, Durham, NC (US); Paul Shoytush, Washington, MI (US)

(73) Assignee: Varian, Inc., Palo Alto, CA (US)

( * ) Notice: Subject to any disclaimer, the term of this patent is extended or adjusted under 35 U.S.C. 154(b) by 635 days.

(21) Appl. No.: 09/795,819

(22) Filed: Feb. 28, 2001

(65) Prior Publication Data

US 2002/0119076 A1 Aug. 29, 2002

(51) Int. Cl.[7] .................. G01N 33/48; G01N 33/00; B01F 7/08; B01F 15/00; B01F 13/08
(52) U.S. Cl. .................. 422/68.1; 73/866; 366/91; 366/95; 366/164.3; 366/245; 366/249; 366/255; 366/279; 366/292; 366/297; 366/325.1
(58) Field of Search .................. 366/91, 95, 100, 366/201, 254, 255, 165.3, 245, 249, 257, 279, 292, 297, 325.1; 422/63, 65, 66, 67, 68.1, 99, 100, 225

(56) References Cited

U.S. PATENT DOCUMENTS

| | | | | |
|---|---|---|---|---|
| 3,787,185 A | * | 1/1974 | Rohrbaugh et al. | 422/64 |
| 4,879,917 A | * | 11/1989 | Eppelmann et al. | 73/866 |
| 5,412,979 A | * | 5/1995 | Fassihi | 73/53.01 |
| 5,682,001 A | * | 10/1997 | Hanson et al. | 73/866 |
| 6,040,192 A | * | 3/2000 | Tuunanen | 436/177 |
| 6,060,024 A | * | 5/2000 | Hutchins et al. | 422/81 |
| 6,170,980 B1 | | 1/2001 | Martin | |
| 6,336,739 B1 | * | 1/2002 | Lee | 366/143 |
| 6,497,157 B1 | * | 12/2002 | Viegas et al. | 73/866 |

FOREIGN PATENT DOCUMENTS

| | | |
|---|---|---|
| EP | 0 121 345 A2 | 10/1984 |
| EP | 0 278 374 A3 | 8/1988 |
| EP | 0 635 713 A1 | 1/1995 |
| EP | 1 052 498 A1 | 11/2000 |
| WO | WO 95/23329 | 8/1995 |

* cited by examiner

*Primary Examiner*—Jill Warden
*Assistant Examiner*—Brian R. Gordon
(74) *Attorney, Agent, or Firm*—David Gloekler; Bella Fishman

(57) ABSTRACT

A dissolution test apparatus comprises a spindle head assembly interconnected between first and second lateral support members. The lateral support members are translatable along a first axis, and the spindle head assembly is translatable along a second axis, such that the spindle head assembly is movable from a front, operative position at which test procedures are effected, to a rear position at which access to the dissolution test apparatus is enhanced. The spindle head assembly includes a dosage delivery mechanism including an actuatable dosage unit-retaining member. A front portion of the dissolution test apparatus has a tapered width to accommodate a triangular or trapezoidal array of test vessels, resulting in high visibility of the vessels.

31 Claims, 24 Drawing Sheets

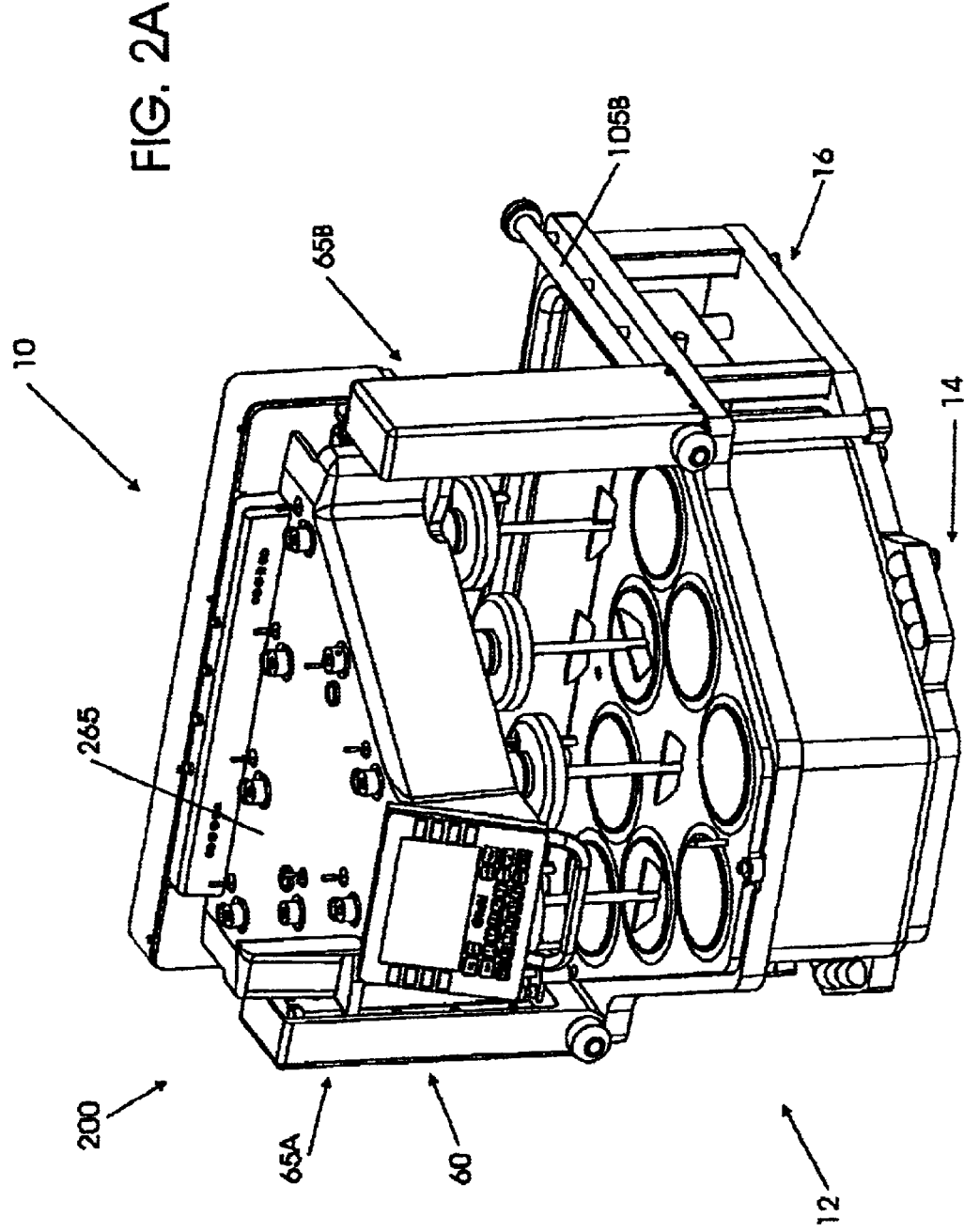

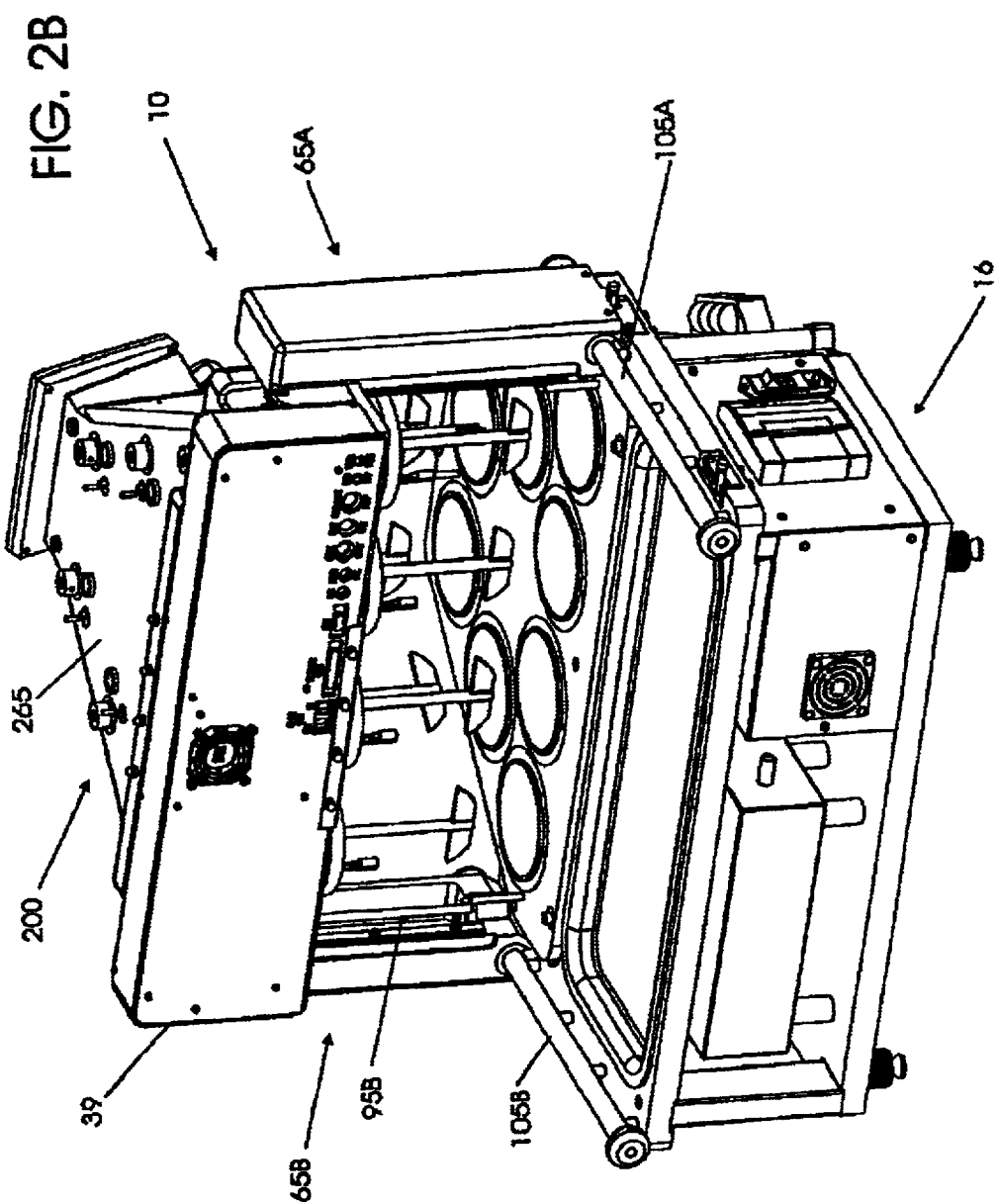

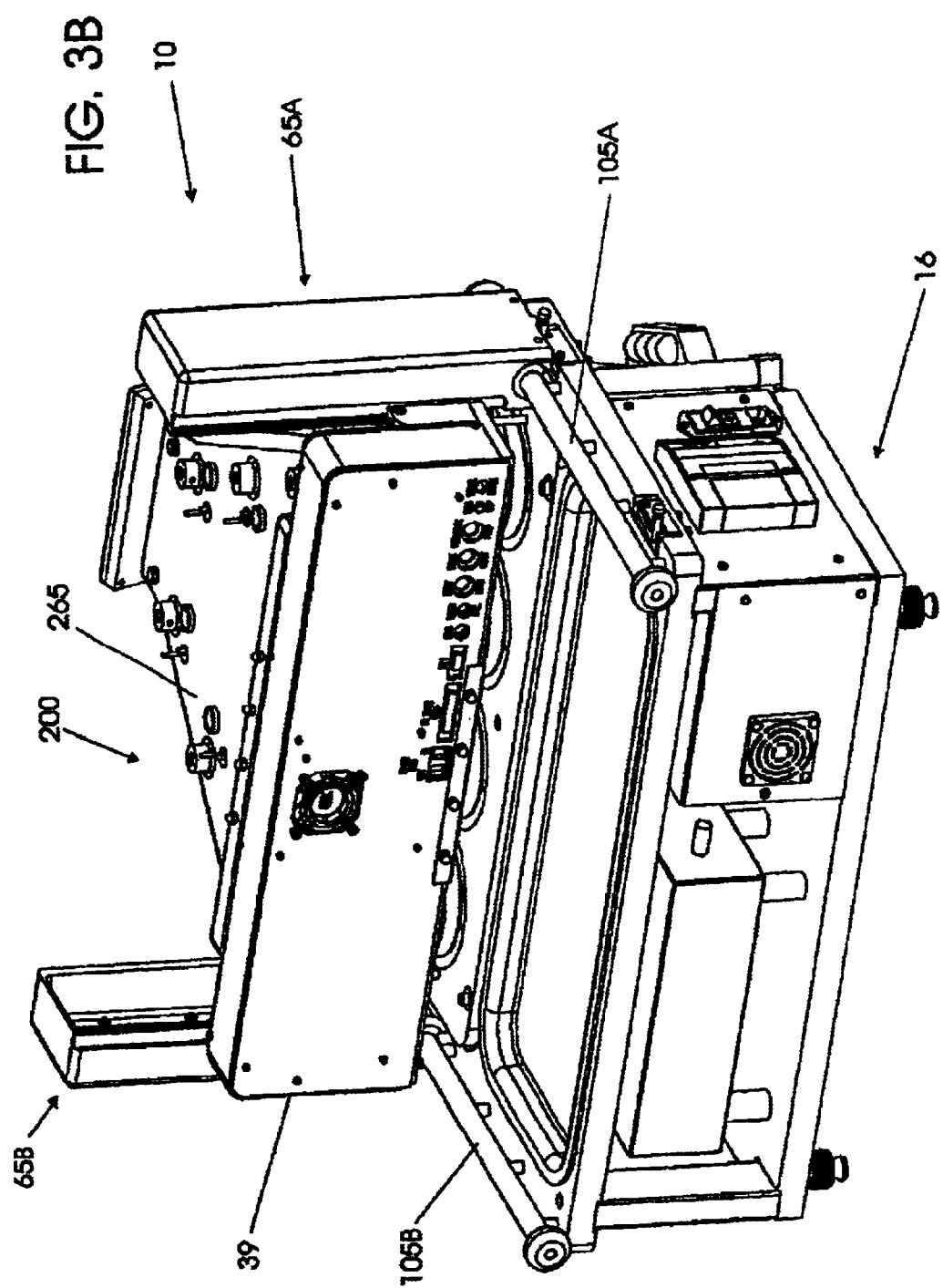

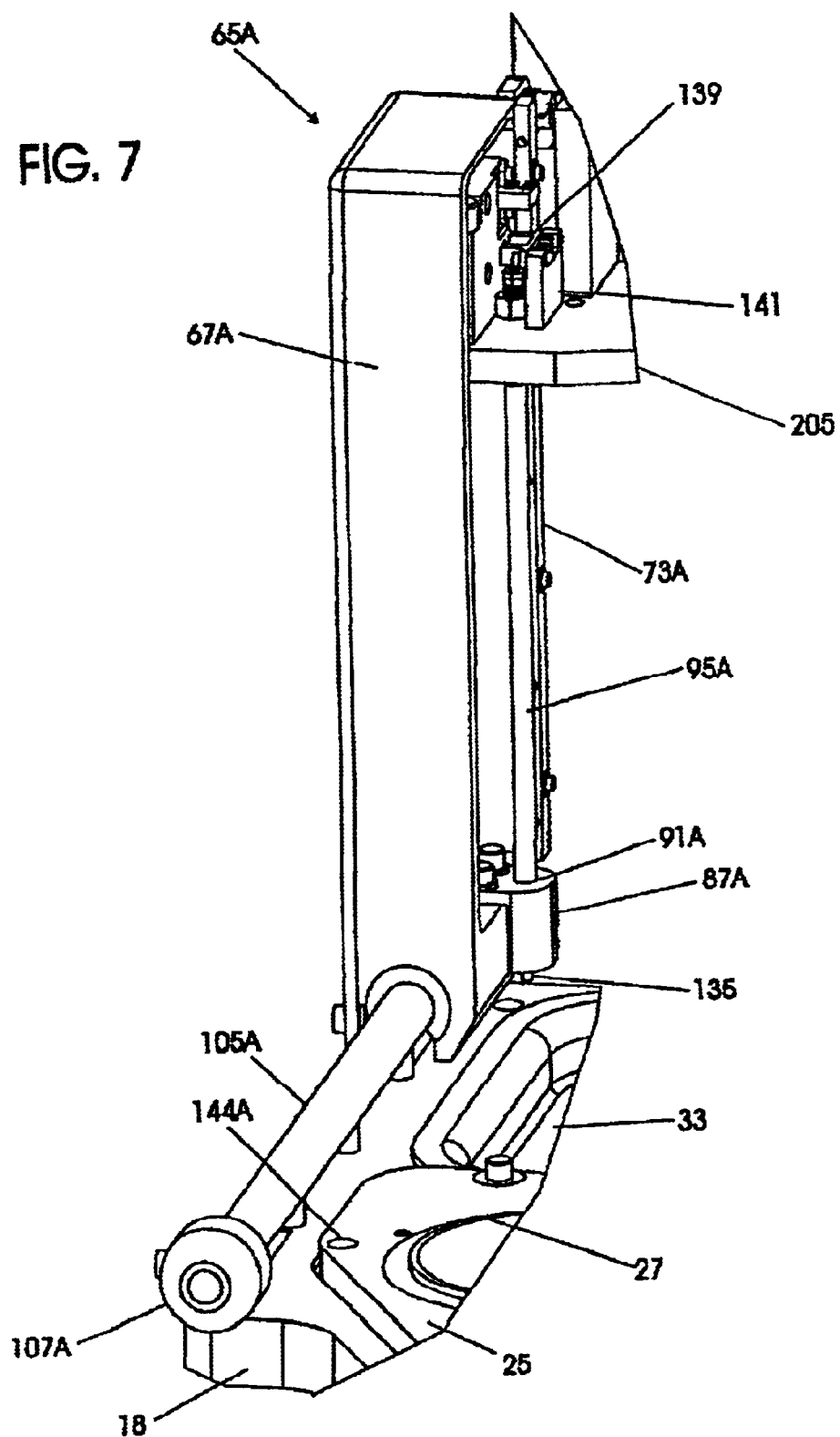

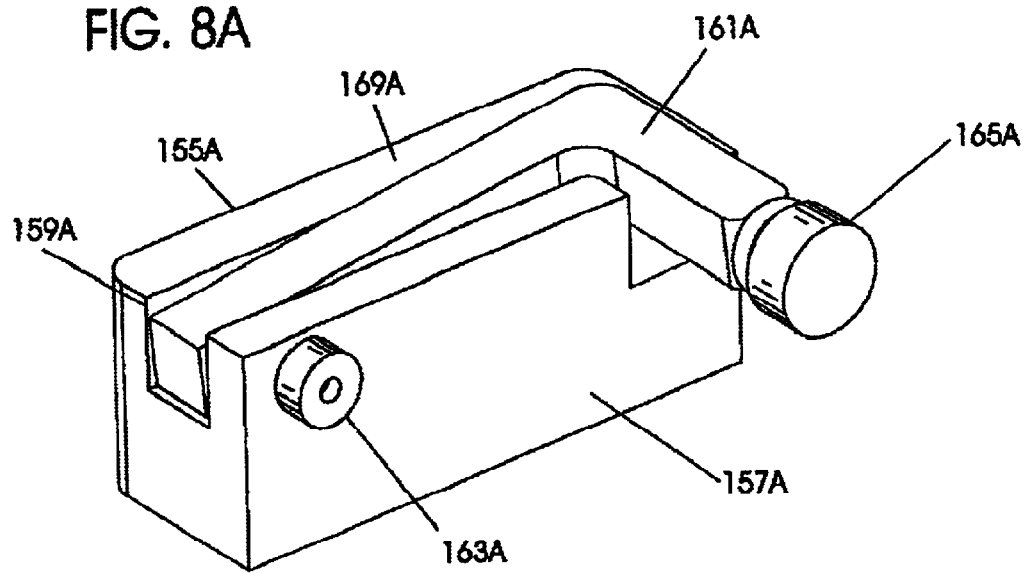
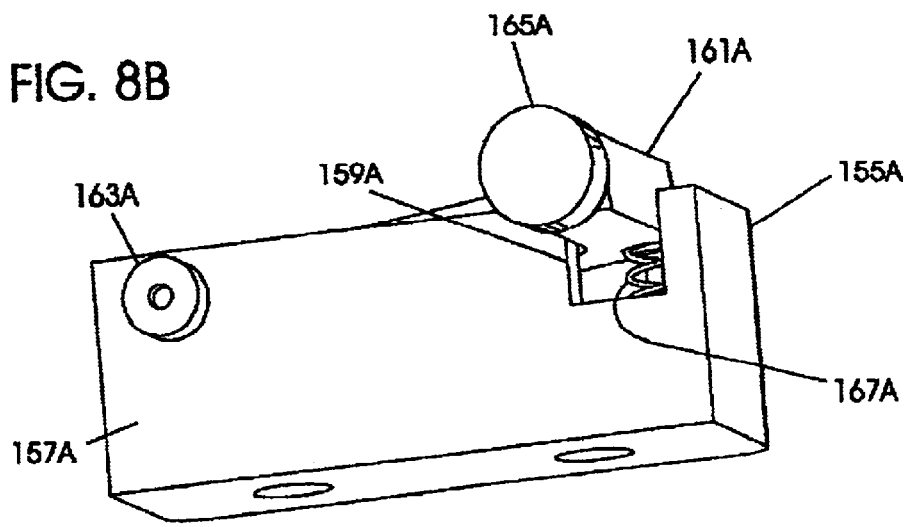

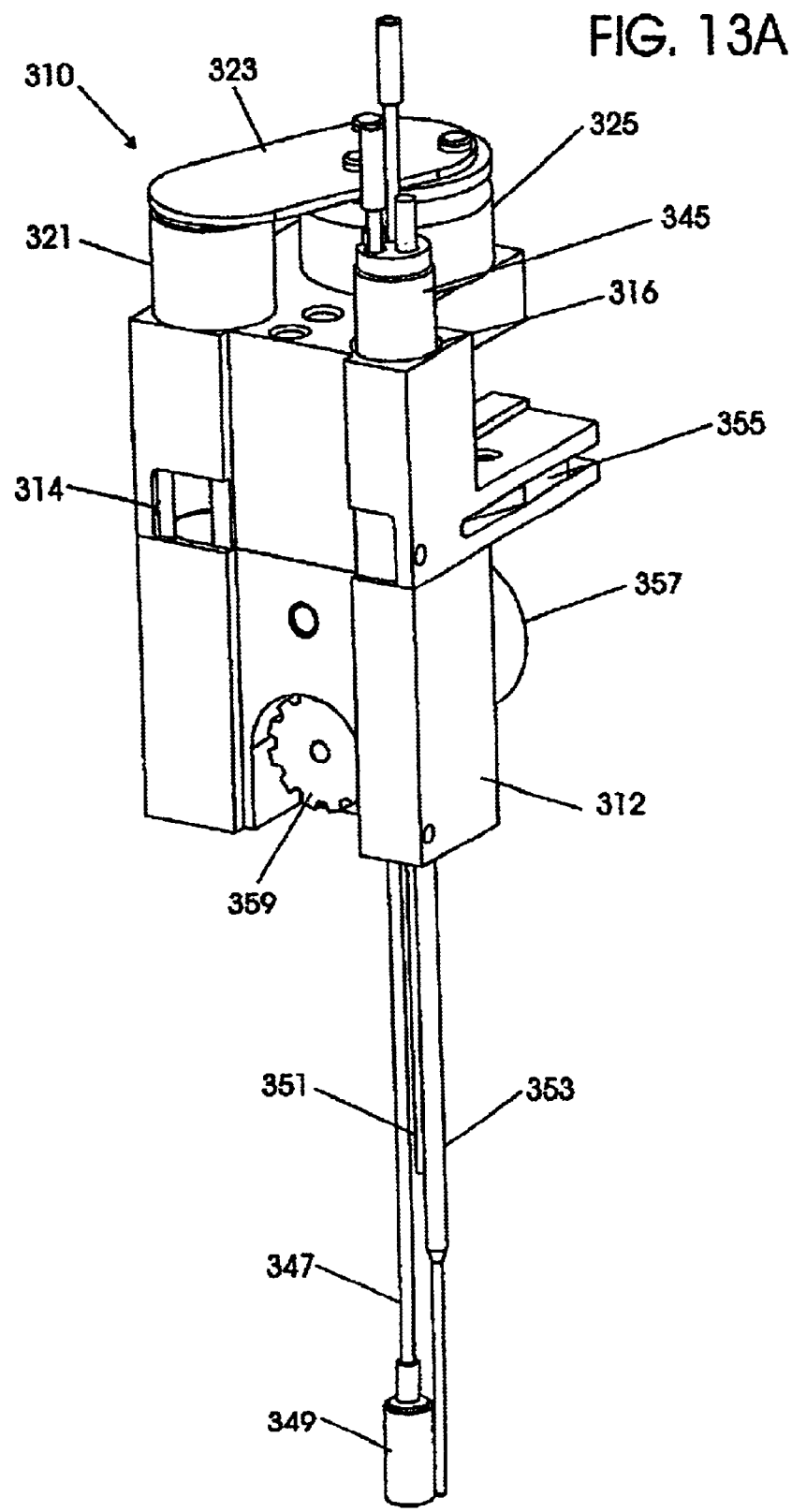

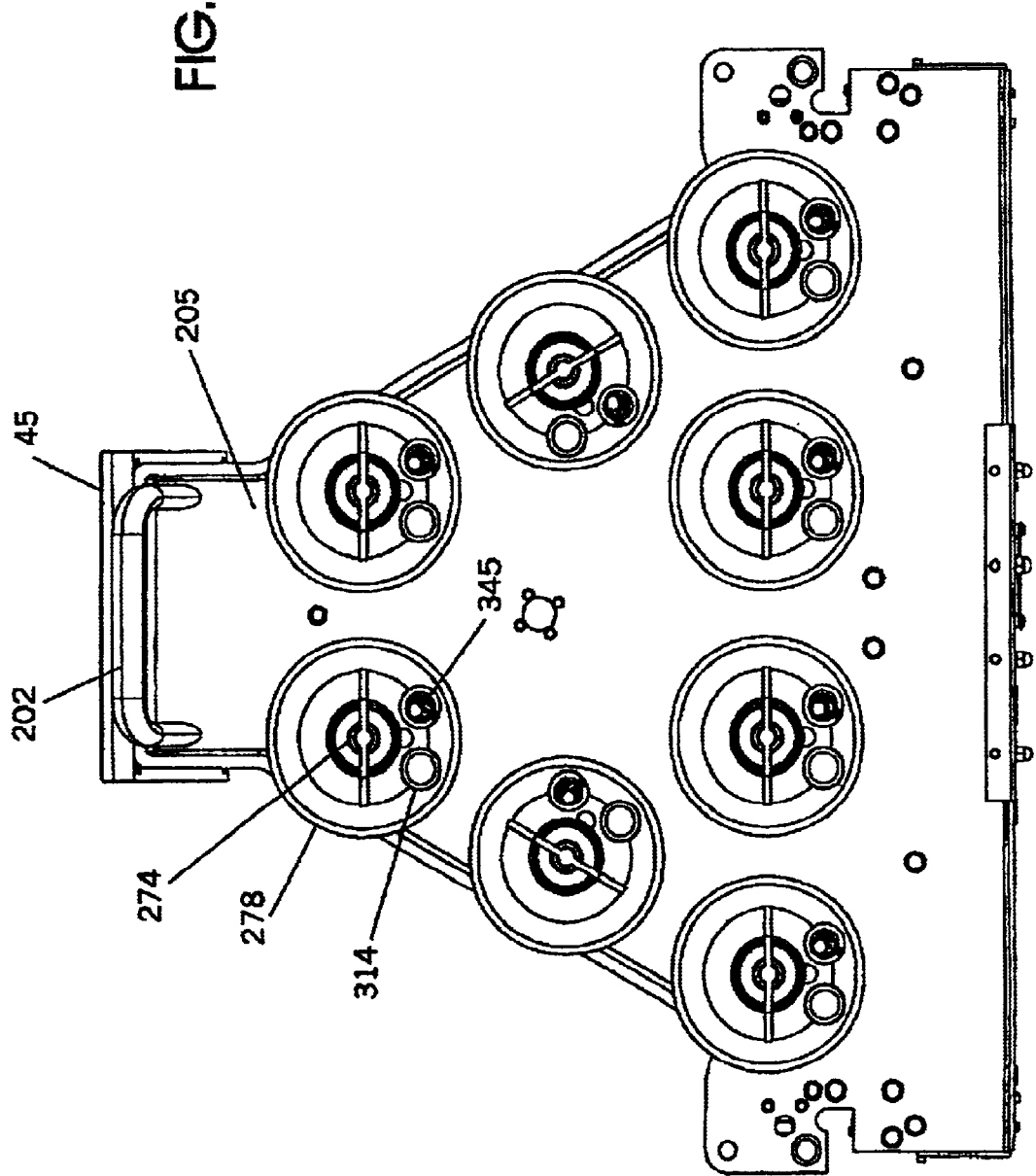

DISSOLUTION TEST APPARATUS

FIELD OF THE INVENTION

The present invention generally relates to dissolution testing and, in particular, apparatus and methods for facilitating and improving dissolution test procedures.

BACKGROUND OF THE INVENTION

Dissolution testing and analysis is required to be performed on sample substances manufactured by participants in various industries, such as the pharmaceutical industry, in order to assess therapeutic efficacy and/or other properties. The sample substances are often provided in the form of dosage units such as tablets, filled capsules, or transdermal patches. During a typical dissolution test procedure, the active components of the dosage units are released into solutions contained in specially designed test vessels under controlled conditions which may or may not be representative of the human digestive process, contact with the skin, or implantation within the body. Dissolution analysis by automated means has become popular for increasing throughput and improving accuracy, precision, reliability, and reproducibility. Automation also relieves the tedium of manually performing a variety of requisite procedures, including: handling and delivering dosage units such as capsules and tablets; monitoring dissolution system parameters; operating the spindle assemblies carrying the agitation paddles or baskets; recording, displaying and printing accumulated data and test results; controlling operations according to predetermined parameters such as time and temperature; and cleaning and filtering the vessels employed in such procedures.

One example of a known automated dissolution testing system is disclosed in U.S. Pat. No. 6,060,024 to Hutchins et al. The vessel rack holds a rectilinear array of six test vessels. The array consists of a front row of three equally-spaced, side-by-side test vessels, and likewise a back row of three equally-spaced, side-by-side test vessels. Separate, individual control heads are respectively mounted onto each test vessel. Each control head includes a housing or cover piece fitted onto a base plate. A number of operative components are mounted to or supported by each housing, including a liquid media sampling line, a retractable sampling probe with a servo motor and transmission components, a temperature detector, a waste aspirate line coupled to a drive assembly, a test vessel wash line, a media fill line, a pH adjustment and media replacement line, a carousel-type sample tablet dispenser coupled to a stepper motor, and an electrical interconnect board with an electrical cable. A paddle shaft extends into each vessel independently from the operative components comprising the control head for that vessel. All paddle shafts are driven by a common paddle drive assembly situated above the control heads.

The structural configuration of automated systems such as that disclosed in U.S. Pat. No. 6,060,024 does not facilitate access into the test vessels, and does not enable a high degree of visibility of the various components operating within the test vessels. In order to provide unobstructed access into the test vessels, the paddle drive assembly must be manipulated to remove each paddle shaft and each control head must be removed from its respective vessel. In addition, the control heads are quite large, so that the paddle drive assembly must be situated at a high elevation with respect to the test vessel. As a result, each paddle shaft is quite long and thus is prone to becoming misaligned in the test vessel or to wobble within the test vessel.

DISCLOSURE OF THE INVENTION

In accordance with one aspect of the present invention, a dissolution test apparatus is provided in which a spindle head assembly integrates a number of components useful in conducting dissolution test procedures. The spindle head assembly is movable between (1) an operative position at which the components of the spindle head assembly can perform operations at test sites, such as provided in the form of an array of test vessels; (2) an intermediate position at which the spindle head assembly is raised above the test sites; and (3) a rear position at which the entire spindle head assembly, and thus its components, are disposed out of the way of the test sites so as to facilitate full access to the test sites. In the context of a multi-vessel dissolution test apparatus, a plurality of groups of components are mounted to the spindle head assembly so as to provide a plurality of fully functional, individual vessel testing modules operative at each corresponding test site. As each component group is mounted to the spindle head assembly, each group moves with the spindle head assembly as the spindle head assembly is transported among its operative, intermediate and rear positions. The spindle head assembly has a low profile. Moreover, when in the operative position, the gap or distance between the spindle head assembly and the test vessel sites is relatively small. As a result of these features, the length of the agitator shafts depending from the spindle head assembly can be made shorter than that provided with conventional systems. The shorter shafts are less prone to wobble or become misaligned.

In accordance with another aspect of the present invention, a dissolution test apparatus is provided in a configuration that improves visibility and accessibility with respect to various components of the dissolution test apparatus. A front section of the dissolution test apparatus is tapered such that the width of the front section narrows in a direction from the rear of the dissolution test apparatus to the front thereof. In this manner, an array of test vessels mounted in the front section can be arranged such that an optimal number of the test vessels are situated along the tapering sides of the front section. This tapered (or triangular or trapezoidal) configuration can be implemented in combination with the movable spindle head assembly described in the preceding paragraph, resulting in enhanced utility of the dissolution test apparatus.

In accordance with a further aspect of the present invention, improved dosage delivery mechanisms are provided, as described hereinbelow. The dosage delivery mechanisms can be advantageously mounted to the spindle head assembly so as to be movable therewith. The dosage delivery mechanisms can be integrated with probe mechanisms, which typically include one or more probes or other instruments operable within test vessels, so as to form combined probe/dosage delivery mechanisms.

According to one embodiment of the present invention, a dissolution test apparatus comprises a frame assembly for supporting a test vessel, a transport assembly, and a spindle head assembly. The frame assembly includes a front section and a rear section. The transport assembly includes first and second lateral support members. Each of the first and second lateral support members includes an upper section and a lower section. Each of the first and second lateral support members is movably mounted to the frame assembly and movable along a first axis to and from the front and rear sections of the frame assembly. The spindle head assembly comprises an operative component for interaction with the test vessel, and is movably connected to each of the first and second lateral support members. The spindle head assembly is movable along a second axis to and from the upper and lower sections of the first and second lateral support members.

According to another embodiment of the present invention, a vessel plate is mounted at the front section of the frame assembly. The vessel plate includes a plurality of apertures defining vessel sites at which test vessels can be mounted. A fluid bath container can be provided under the vessel plate, so that the test vessels can be immersed in a heated bath. Alternatively, each vessel can be individually and directly heated by providing modified vessels to which heater elements are placed in thermal contact.

According to yet another embodiment of the present invention, a dissolution test apparatus comprises a frame assembly, a vessel plate, and a spindle head assembly. The vessel plate is supported by the frame assembly and includes a plurality of apertures defining vessel sites. The spindle head assembly is supported by the frame assembly and is movable between a front lowered position, a front raised position and a rear position. The spindle head assembly includes a plurality of rotatable shafts, a plurality of dosage delivery mechanisms and a plurality of probe mechanisms. The spindle head assembly at the front raised position is disposed above the vessel plate. The spindle head assembly at the rear position is disposed in an offset, non-obstructive relation to the vessel sites. At the front lowered position of the spindle head assembly, each of the rotatable shafts, each of the dosage delivery mechanisms and each of the probe mechanisms, respectively, is operatively aligned with a corresponding one of the vessel sites.

According to still another embodiment of the present invention, a dissolution test apparatus comprises a frame assembly including a front section and a rear section, a first axis transport assembly mounted to the frame assembly, a second axis transport assembly movably engaging the first axis transport assembly, and a spindle head assembly. The spindle head assembly includes a plurality of rotatable shafts, a plurality of dose delivery mechanisms and a plurality of sampling probe assemblies. The spindle head assembly is movably supported by the second axis transport assembly between a front lowered position and a front raised position, and the spindle head is assembly movable with the first axis transport assembly between a rear position and the front raised position. The spindle head assembly at the front lowered position is disposed above the front section of the frame assembly, and at the rear position is disposed above the rear section of the frame assembly.

According to a further embodiment of the present invention, a dissolution test apparatus comprises a frame assembly, a vessel plate and a spindle head assembly. The frame assembly includes a front section and a rear section. The front section has first and second laterally spaced edges defining a tapered width of the front section. The tapered width narrows in a direction from the rear section to the front section. The vessel plate is mounted at the front section and includes a plurality of vessel mounting apertures. At least a majority of the apertures are disposed along first and second vessel alignment directions, with the first vessel alignment direction running parallel to the first edge of the front section and the second vessel alignment direction running parallel to the second edge of the front section. The spindle head assembly is supported by the frame assembly and including a plurality of rotatable shafts.

According to a yet further embodiment of the present invention, a dissolution test apparatus comprises a frame assembly including a front section and a rear section, a vessel plate mounted at the front section, and a spindle head assembly supported by the frame assembly and including a plurality of rotatable shafts. The vessel plate includes first and second laterally spaced edges defining a tapered width of the vessel plate. The tapered width narrows in a direction from the rear section to the front section. The vessel plate further includes a plurality of vessel mounting apertures. At least a majority of the apertures are disposed along first and second vessel alignment directions, with the first vessel alignment direction running parallel to the first edge of the vessel plate and the second vessel alignment direction running parallel to the second edge of the vessel plate.

According to a still further embodiment of the present invention, a dissolution test apparatus comprises a frame assembly for supporting a test vessel, first and second lateral support members, and a spindle head assembly. The frame assembly includes a front section and a rear section. The first and second lateral support members are movably mounted to the frame assembly for movement between the front and rear sections along a first axis. Each of the first and second lateral support members includes an upper section and a lower section. The spindle head assembly comprises an operative component for interaction with the test vessel, and is connected to the first and second lateral support members for movement therewith along the first axis. The spindle head assembly is movable along a second axis to and from the upper and lower sections of the first and second lateral support members.

According to an additional embodiment of the present invention, the spindle head assembly includes an elongate spindle head guide member having upper and lower ends. The spindle head guide member depends downwardly from the spindle head assembly, and its upper end is supported by the spindle head assembly. A lift rod is movably disposed in the spindle head guide member and includes an upper end and a lower end. A lift rod position sensor is operatively aligned with the upper end of the lift rod, and is adapted to detect upward movement of the lift rod with respect to the elongate spindle head guide member.

According to another embodiment of the present invention, a dissolution test apparatus comprises a frame assembly, a transport assembly, and a spindle head assembly including a dose delivery mechanism. The frame assembly includes a front section and a rear section. The transport assembly includes first and second lateral support members. Each of the first and second lateral support members includes an upper section and a lower section. Each of the first and second lateral support members is movably mounted to the frame assembly, and is movable along a first axis to and from the front and rear sections of the frame assembly. The spindle head assembly is interposed between the first and second lateral support members, and is movably connected to each of the first and second lateral support members. The spindle head assembly is movable along a second axis to and from the upper and lower sections of the first and second lateral support members.

The dose delivery mechanism includes a dose delivery conduit, an actuator, and a dosage-retaining element. The dose delivery conduit has a first open conduit end and a second conduit end, and defines a dosage delivery passage. The dosage-retaining element is operatively connected to the actuator, and is movable between a closed state and an open state. In the closed state, the dosage-retaining unit obstructs the dosage delivery passage. In the open state, the dosage-retaining unit is disposed in non-obstructive relation to the dosage delivery passage.

According to yet another embodiment of the present invention, a dissolution test apparatus comprises a frame assembly, a vessel plate supported by the frame assembly and including a plurality of vessel locations, and a spindle head assembly. The spindle head assembly is supported by the frame assembly and is movable between a front position and a rear position. The spindle head assembly includes a plurality of dose delivery mechanisms. Each dose delivery mechanism includes a dose delivery conduit, an actuator, and a dose-retaining element. The dose delivery conduit defines a dose delivery passage, and has a first open conduit end and a second open conduit end. The dose-retaining element is operatively connected to the actuator, and is rotatable between a dose retaining position and a dose delivery position. The dose retaining element blocks the dose delivery passage at the dose retaining position, and opens the dose delivery passage at the dose delivery position. At the front position of the spindle head assembly, the second open conduit end of each of the dose delivery mechanisms is operatively aligned with a corresponding one of the vessel locations. At the rear position of the spindle head assembly, each of the dose delivery mechanisms is disposed in an offset, non-obstructive relation to the vessel plate.

According to still another embodiment of the present invention, a combined probe/dosage delivery mechanism comprises a dose delivery conduit, an actuator, a dosage retaining element, a probe member bore, a probe member movably disposed in the probe member bore, a probe drive motor, and a probe drive transmission mechanism. The dose delivery conduit has a first open conduit end and a second conduit end, and defines a dosage delivery passage. The dosage-retaining element is operatively connected to the actuator. The dosage-retaining element is movable between a closed state wherein the dosage-retaining unit obstructs the dosage delivery passage, and an open state wherein the dosage-retaining unit is disposed in non-obstructive relation to the dosage delivery passage. The probe drive transmission mechanism is operatively coupled between the probe drive motor and the probe member.

It is therefore an object of the present invention to provide an improved dissolution test apparatus.

It is another object of the present invention to provide a dissolution test apparatus wherein several components adapted for insertion into and extraction from one or more test vessels are integrated into a single spindle head assembly.

It is yet another object of the present invention to provide a dissolution test apparatus in which a spindle head assembly is movable between a first position wherein the components of the spindle head assembly are operatively aligned with test sites, and a second position wherein the components offset from the test sites and accordingly enhance access to the test sites.

It is still another object of the present invention to provide a dissolution test apparatus including an array of test sites such as mounting locations for test vessels, wherein the dissolution test apparatus is structured so as to enable a high degree of accessibility to and visibility of the test sites.

It is a further object of the present invention to provide improved devices for the delivery of dosage units such as tablets to test vessels, and for the probing and/or sampling of media contained in the test vessels.

It is an additional object of the present invention to provide an integrated unit that exhibits both dosage delivery and probing functions.

Some of the objects of the invention having been stated hereinabove, other objects will be evident as the description proceeds, when taken in connection with the accompanying drawings as best described hereinbelow.

BRIEF DESCRIPTION OF THE DRAWINGS

FIG. 2A is a front perspective view of the dissolution test apparatus illustrated in a front raised position in accordance with the present invention;

FIG. 2B is a rear perspective view of the dissolution test apparatus illustrated in FIG. 2A;

FIG. 3B is a rear perspective view of the dissolution test apparatus illustrated in FIG. 3A;

FIG. 7 is a front perspective view of the movable support member illustrated in FIG. 4 operatively attached to the spindle head assembly and the frame of the dissolution test apparatus in accordance with the present invention;

FIG. 8A is a perspective view of a latch assembly provided with the dissolution test apparatus in accordance with the present invention;

FIG. 8B is another perspective view of the latch assembly illustrated in FIG. 8A;

FIG. 13A is a perspective view of a combined probe/dosage delivery mechanism provided with the dissolution test apparatus in accordance with the present invention;

FIG. 14 is a bottom plan view of the spindle head assembly provided with the dissolution test apparatus in accordance with the present invention;

DETAILED DESCRIPTION OF THE INVENTION

Figure 1A:
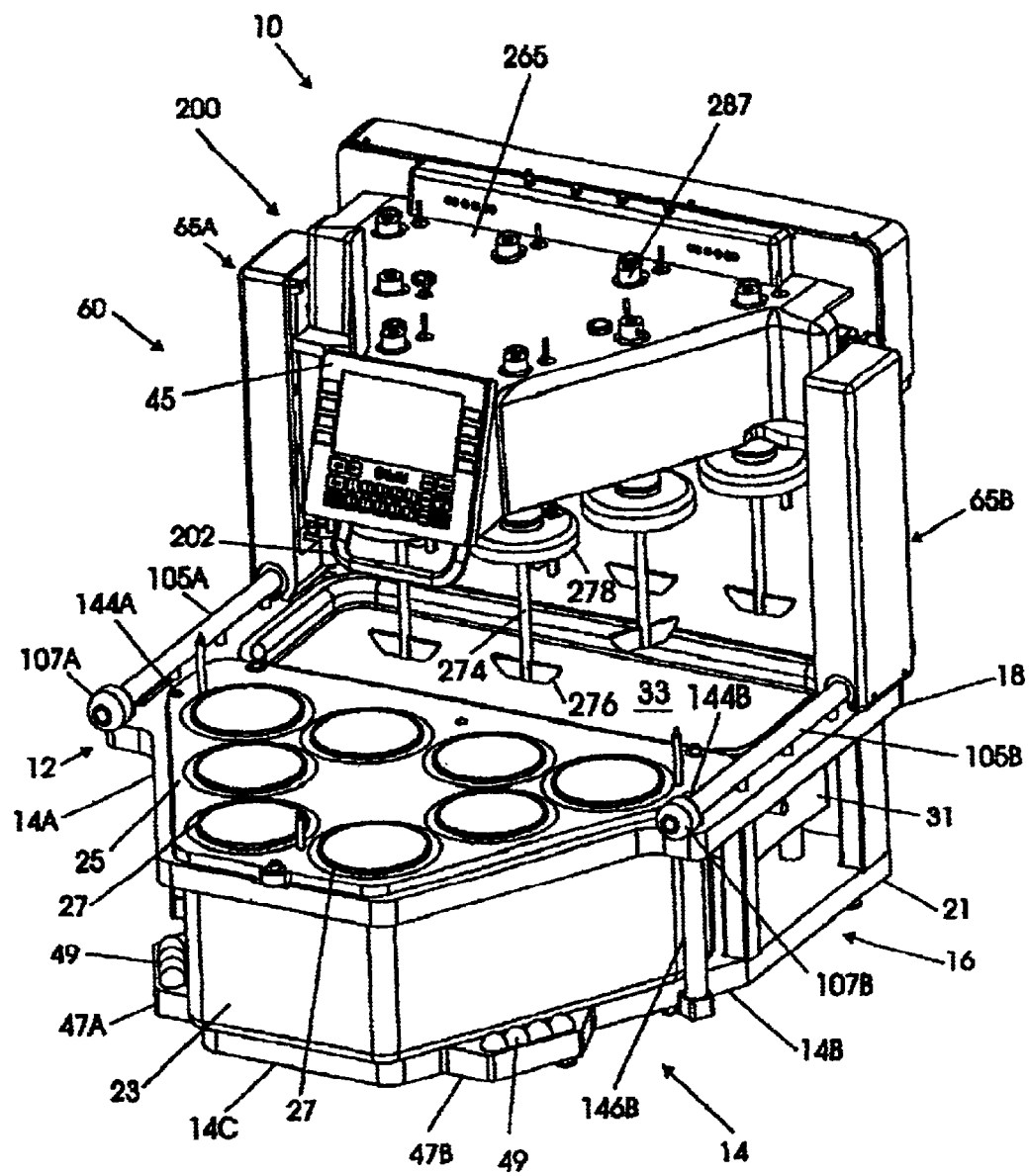
FIG. 1A is a front perspective view of a dissolution test apparatus illustrated in a rear position in accordance with the present invention.
Figure 1B:
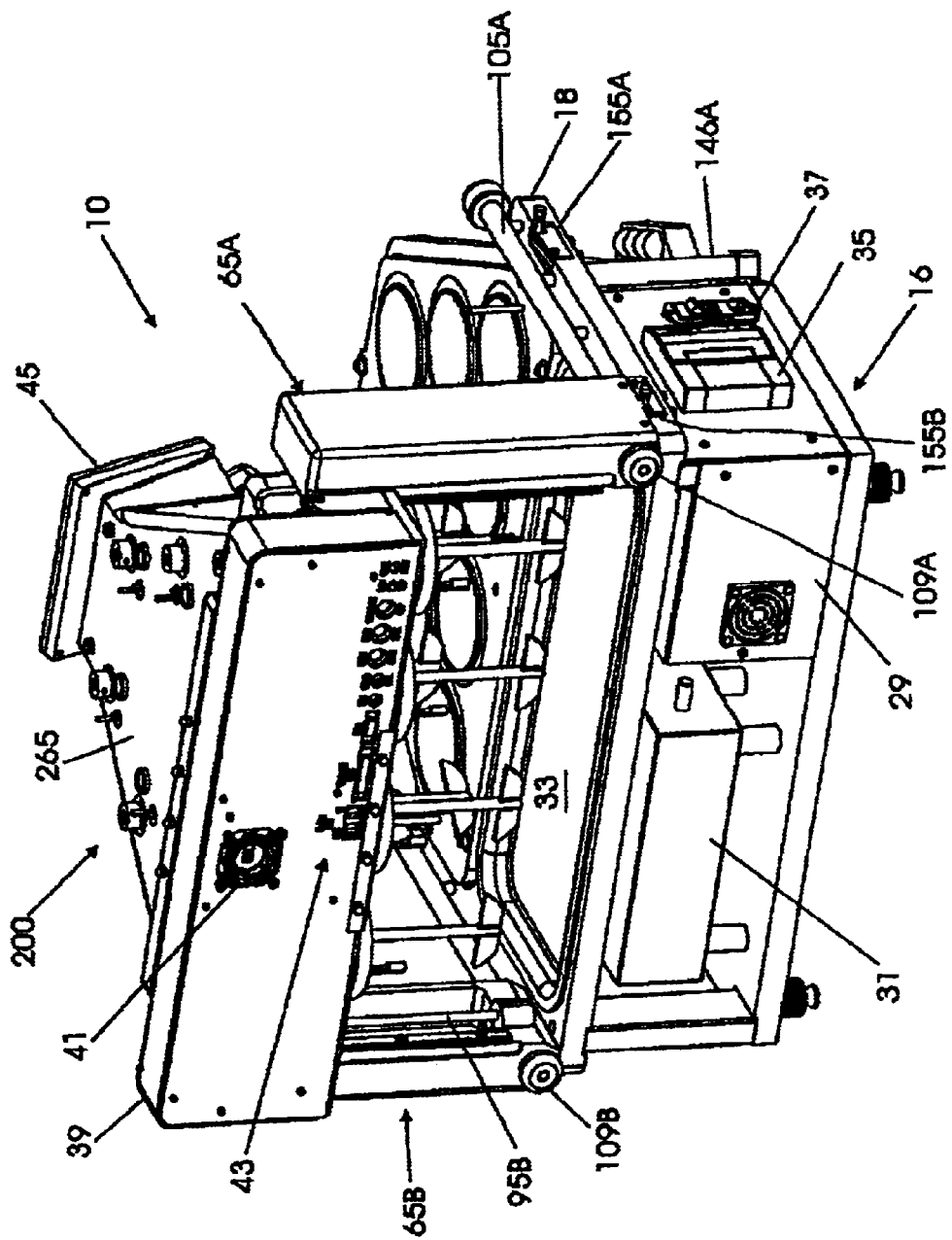
FIG. 1B is a rear perspective view of the dissolution test apparatus illustrated in FIG. 1A.

Referring now to FIGS. 1A and 2A, an automated dissolution test apparatus, generally designated 10, is illustrated in accordance with the present invention. Dissolution test apparatus includes a frame assembly, generally designated 12, having a front section, generally designated 14, and a rear section, generally designated 16. The structure defining frame assembly 12 includes an upper plate 18 and a lower or base plate 21. In front section 14, a water bath container 23 is interposed between upper and lower plates 18 and 21, and a vessel plate 25 is mounted on upper plate 18. Vessel plate 25 has a plurality of mounting apertures to enable vessel plate 25 to hold a plurality of test vessels 27 that extend into the interior of water bath container 23. Test vessels 27 are preferably of the industry-acceptable type, as understood by persons skilled in the art. Water bath container 23 is adapted to contain a water bath (or a volume of some other suitable heat transfer medium) for regulating the temperature of media held in test vessels 27 at a predetermined temperature. As shown in FIG. 1B, a power box 29 for supplying electrical power to various operative components of dissolution test apparatus 10 is mounted in rear section 16 of dissolution test apparatus 10. In addition, a combined water heater/pump unit 31 is mounted in rear section 16. Heater/pump unit 31 includes appropriate fluid input and output components (not specifically shown) for circulating heated water (or other heat transfer medium) through the interior of water bath container 23 to maintain the desired test vessel media temperature. Heater/pump unit 31 is preferred for its compact design, although it will be understood that separate heater and pump devices could be employed in the present embodiment. Power box 29 and heater/pump unit 31 are both disposed below a drip pan 33 that is removable from rear section 16.

A primary operative assembly of dissolution test apparatus 10 is a spindle head assembly, generally designated 200. Spindle head assembly 200 advantageously integrates, houses and/or supports a number of operative components. In broad terms, spindle head assembly 200 includes, among other components, a plurality of test vessel agitation devices, sampling and temperature probe devices, and sample substance dosage delivery devices, all of which are more fully described hereinbelow. Preferably, the number of such devices associated with spindle head assembly 200 corresponds to the number of test vessels 27 supported by vessel plate 25. For the purposes of the present disclosure, the terms "probe," "probe device," "probe mechanism," "sampling device" and "sampling mechanism" are used interchangeably to refer to a device that includes one or more probes or instruments. Examples of the probes or instruments include one or more cannulae for aspirating or withdrawing fluid from a test vessel 27, and/or for dispensing or returning fluid to a test vessel 27, and further includes temperature probes and fiber optic probes for operative insertion into a test vessel 27.

As shown in FIG. 1A, each test vessel agitation device includes a rotatable agitator shaft 274 equipped with an agitation element such as a paddle 276, although it will be understood that other types of agitation elements could be provided. Alternatively, a basket or other suitable element that is supported at the lower end of agitator shaft 274 could be substituted for paddle 276 in order to hold certain types of sample dosages intended for dissolution within test vessels 27. As further shown in FIG. 1A, spindle head assembly 200 also supports a plurality of evaporation covers 278. When lowered onto the open top ends of test vessels 27 (see FIG. 3A), evaporation covers 278 seal off the respective interiors of test vessels 27 to a degree sufficient to substantially prevent undue loss of gaseous phase media from test vessels 27 during operation of dissolution test apparatus 10, as well as to prevent degradation of the various operative components of spindle head assembly 200 due to condensation from sources escaping from test vessels 27. As will become evident from the remainder of the disclosure herein, the integration of the various devices utilized in dissolution testing procedures into a single spindle head assembly 200 significantly increases the utility of dissolution test apparatus 10 as a research tool.

Figure 3A:
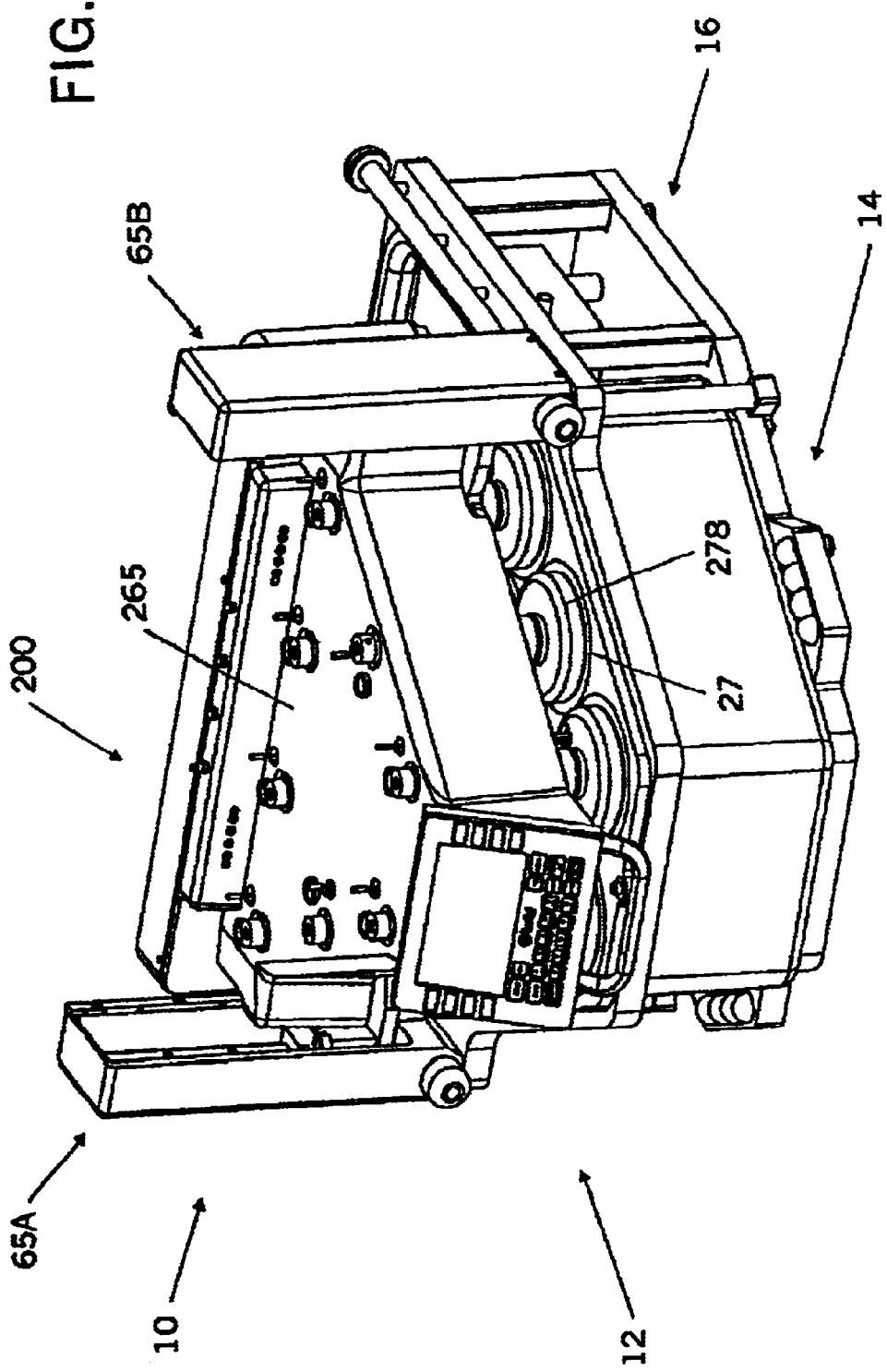
FIG. 3A is a front perspective view of the dissolution test apparatus illustrated in a front lowered position in accordance with the present invention.

Spindle head assembly 200 in its entirety is movably connected to frame assembly 12 through a spindle head transport assembly, generally designated 60. This is another aspect of dissolution test apparatus 10 that significantly increases its utility. The path of travel of spindle head assembly 200 is sequentially illustrated with reference to the front perspective views of FIGS. 1A, 2A and 3A, respectively, or alternatively with reference to the rear perspective views on FIGS. 1B, 2B and 3B. FIGS. 1A and 1B illustrate spindle head assembly 200 in its non-operative or rear position, at which position spindle head assembly 200 is generally disposed above rear section 16 of frame assembly 12 and provides unobstructed access and visibility to vessel plate 25, test vessels 27, and water bath container 23. In this rear position, entire vessel plate 25 can be easily removed to provide access into water bath container 25 to facilitate cleaning of water bath container 25. FIGS. 2A and 2B illustrate spindle head assembly 200 in its intermediate or front raised position, at which position spindle head assembly 200 is generally disposed above front section 14 of frame assembly 12. In its rear position and front raised position, the various components of spindle head assembly 200 do not perform operations within test vessels 27. FIGS. 3A and 3B illustrate spindle head assembly 200 in its operative or front lowered position, at which position spindle head assembly 200 is lowered such that evaporation covers 278 contact and cover the open tops of corresponding test vessels 27. In the front lowered position, agitation shafts 274 and their respective paddles 276 (see, e.g., FIG. 1A) as well as other components of spindle head assembly 200 can operate within test vessels 27.

Referring again to FIGS. 1–3, spindle head transport assembly 60 is preferably provided in the form of a movable upright "goalpost" configuration. In broad terms, spindle head transport assembly 60 includes left and right upright lateral or vertical support members, generally designated 65A and 65B, respectively, spaced from each other on each side of frame assembly 12. Spindle head assembly 200 is movably interconnected between left and right lateral support members 65A and 65B, and is mechanically raised and lowered along lateral support members 65A and 65B in a generally vertical direction. The automated vertical travel of spindle head assembly 200 along lateral support members 65A and 65B enables movement of spindle head assembly 200 between its front raised position (see FIGS. 2A and 2B) and its front lowered position (see FIGS. 3A and 3B). The details of the interaction between spindle head assembly 200 and lateral support members 65A and 65B are described more fully hereinbelow. Left and right lateral support members 65A and 65B (and thus spindle head assembly 200) are movably supported on left and right horizontally-oriented lateral slide rails 105A and 105B, respectively. The front end of each lateral slide rail 105A and 105B includes a front stop member 107A and 107B, respectively, and the rear end of each lateral slide rail 105A and 105B likewise includes a rear stop member 109A and 109B, respectively (see also FIG. 19). For each lateral support member 65A and 65B, front stop members 107A and 107B and rear stop members 109A and 109B respectively provide the forward-most and rearward-most limits of travel along lateral slide rails 105A and 105B. The horizontal travel of lateral support members 65A and 65B (and thus that of spindle head assembly 200) along lateral slide rails 105A and 105B enables movement of spindle head assembly 200 between its rear position (see FIGS. 1A and 1B) and its front raised position (see FIGS. 2A and 2B).

At the present time, it is believed that dissolution test apparatus 10 provides the most efficiency and facility in use when movement of spindle head assembly 200 between the rear position and the front raised position is effected by manual manipulation by the operator of dissolution test apparatus 10. For this purpose, a handle 202 is attached to spindle head assembly 200 as shown in FIGS. 1A, 2A and 3A. It will be understood, however, that movement of spindle head assembly 200 between the rear position and the front raised position could be automated through the utilization of appropriate motorized drive and transmission means, if desired.

Figure 11:
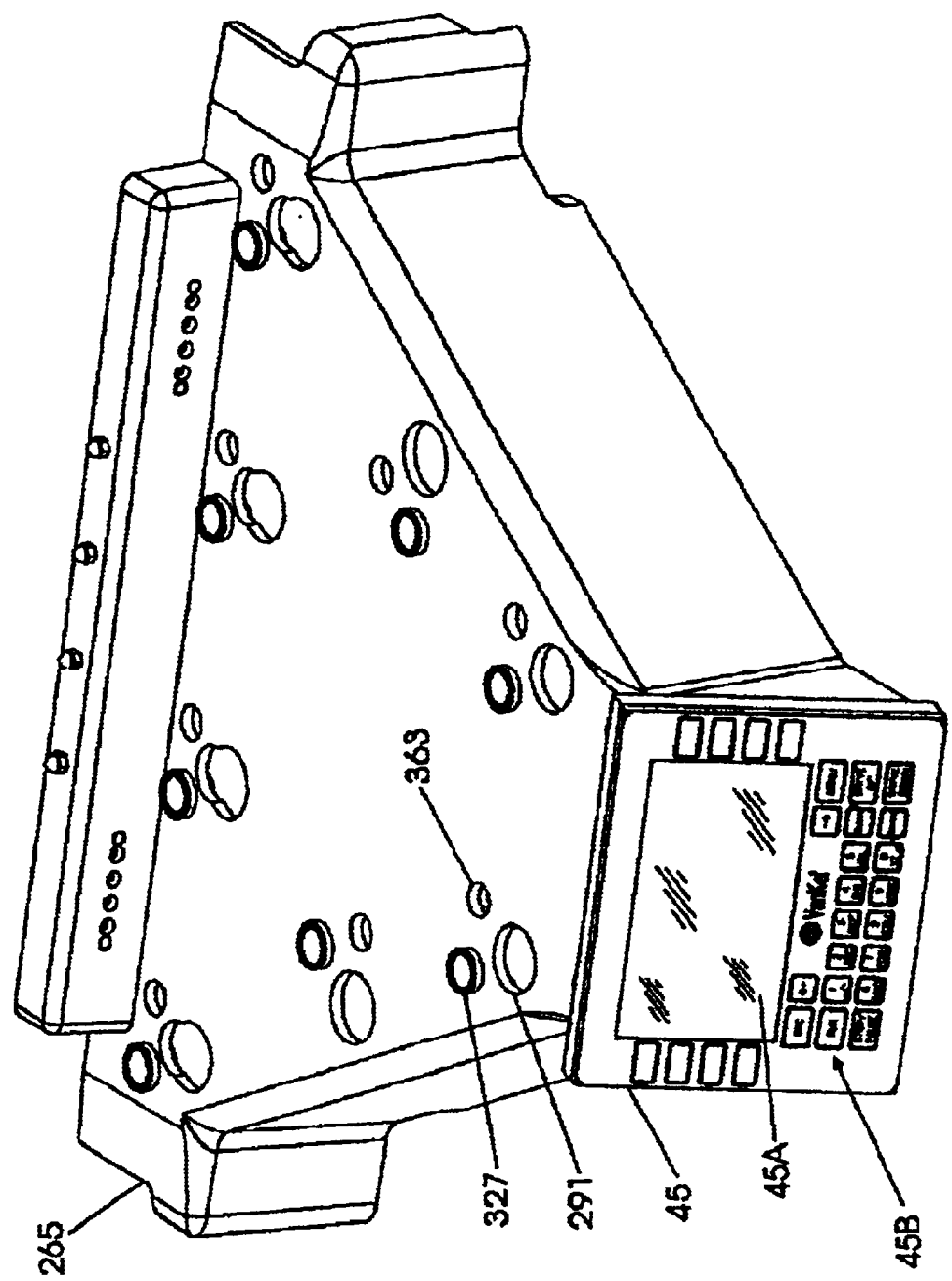
FIG. 11 is a perspective view of a cover for the spindle head assembly illustrated in FIG. 10, including a control panel provided with the dissolution test apparatus in accordance with the present invention.

Dissolution test apparatus 10 further includes other components illustrated in FIGS. 1–3. As shown in FIGS. 1B, 2B and 3B, a data output peripheral device such as an on-board printer device 35 for hard-copy data archival, and a master ON/OFF power switch 37 for dissolution test apparatus 10, are each mounted at one side of rear section 16 of dissolution test apparatus 10. A rear housing 39 of dissolution test apparatus 10, which may or may not be movable with spindle head assembly 200, includes a cooling fan unit 41 and a group of fluid and/or electrical input and output connections, generally designated 43. As shown in FIGS. 1A, 2A and 3A, dissolution test apparatus 10 includes an input/output interface in the form of a control panel 45 communicating with an associated programmable systems control module (not specifically shown). As best shown in FIG. 11, control panel 45 includes a display device such as an LCD (liquid crystal display) screen 45A and a number of alphanumeric and/or symbolic keypads, generally designated 45B. Keypads 45B enable an operator of dissolution test apparatus 10 to input a variety of dissolution test parameters and operational instructions, as well as commands for movement of spindle head assembly 200. The operator can use keypads 45B to write a complete program or set of instructions to be executed by dissolution test apparatus 10. Preferably, control panel 45 and its associated operative components are integrated into spindle head assembly 200.

As best shown in FIGS. 1A, 2A and 3A, a rack 47A or 47B is respectively formed or attached to each tapered side of lower plate 21 of frame assembly 12. Each rack 47A and 47B holds a plurality of precisely dimensioned balls 49 for use in ensuring that dissolution test apparatus 10 is operating in accordance with USP standards. Specifically, balls 49 are used to ensure that each agitator shaft 274 is correctly positioned in relation to the lowermost inside surface of each corresponding test vessel 27. As with other procedures involving the use of dissolution test apparatus 10, this calibration procedure is greatly facilitated by the movable, integrated design of spindle head assembly 200. That is, when spindle head assembly 200 is in the rear position shown in FIGS. 1A and 1B, each ball 49 can be easily dropped into each test vessel 27. Spindle head assembly 200 is then moved through the intermediate, front raised position shown in FIGS. 2A and 2B, and ultimately into the operative, front lowered position shown in FIGS. 3A and 3B, at which point each agitator shaft 274 has been lowered into its associated test vessel 27. To properly calibrate the position of each agitator shaft 274, each is adjusted until its lowermost end surface (which may be the bottom surface of paddle 276) contacts a ball 49. In this manner, the height of each agitator shaft 274 in relation to the bottom of its test vessel 27 is brought into compliance with USP requirements.

Figure 19:
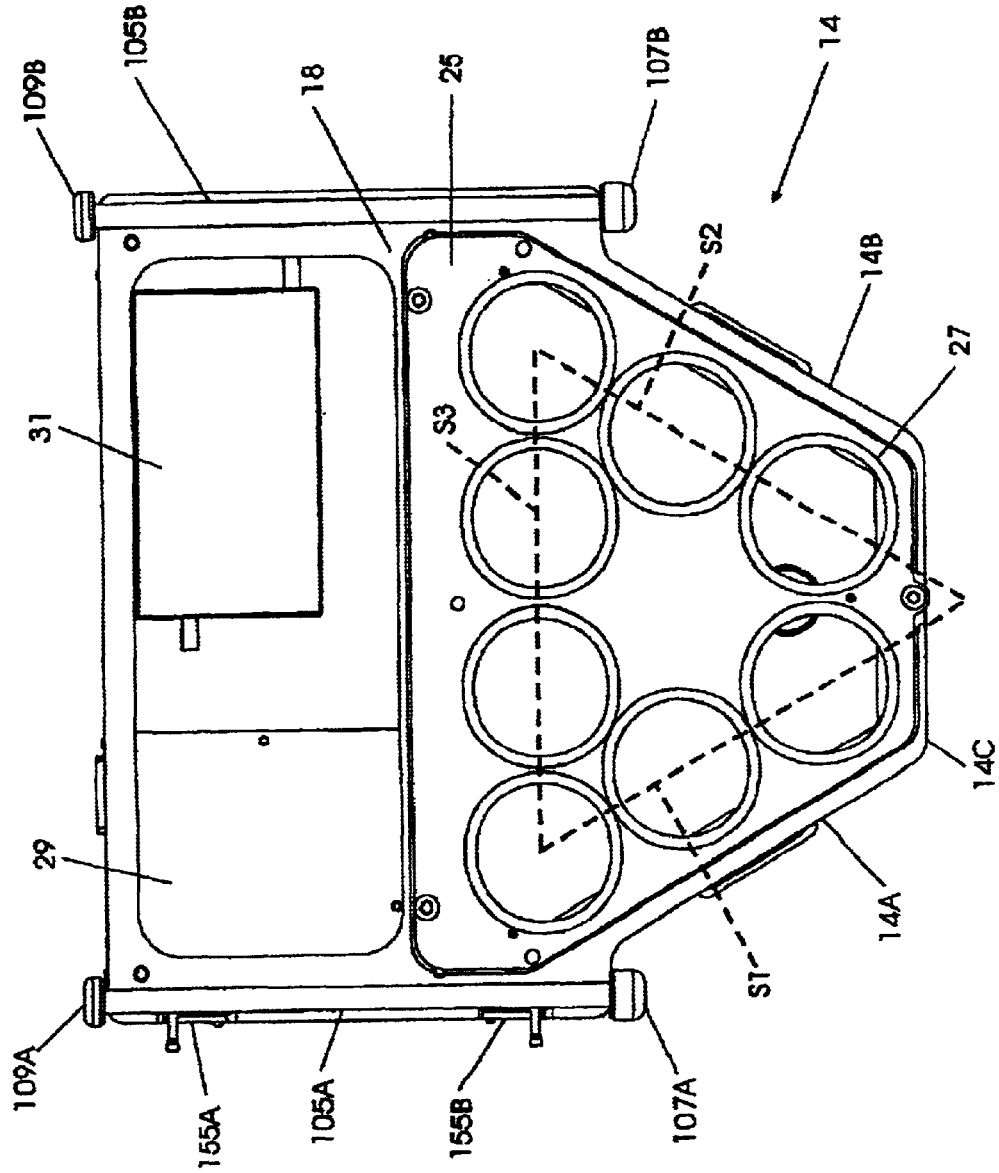
FIG. 19 is a top plan view of the dissolution test apparatus illustrated in FIGS. 1–3 with the spindle head assembly removed.

As shown in FIGS. 1A, 2A and 3A, and as further shown in FIG. 19, front section 14 of frame assembly 12 is tapered such that its width varies and narrows in the general direction from the rear of dissolution test apparatus 10 to the front of dissolution test apparatus 10. Equivalently, front section 14 could be described as being triangular or trapezoidal. Hence, front section 14 preferably has at least two sides or edges 14A and 14B defining the tapered width, and can also have a front side or edge 14C at which sides 14A and 14B terminate. The tapered profile can be implemented, for example, by tapering the area of the front region of upper plate 18 and/or vessel plate 25. Hence, sides or edges 14A, 14B and 14C could be represented by the sides or edges of either upper plate 18, vessel plate 25, or both upper plate 18 and vessel plate 25. That is, the tapered configuration could be defined by either varying an area of upper plate 18 and/or an area of vessel plate 25.

This configuration enables a tapered, triangular or trapezoidal array of test vessels 27, and is best implemented with the use of four or more (e.g., eight) test vessels 27. The arrangement results in the maximum number of test vessels 27 being situated generally along sides 14A and 14B of front section 14. In the embodiment illustrated in FIGS. 1–3 and 19, three test vessels 27 are situated along each side 14A and 14B. As specifically shown in FIG. 19, the test vessel array forms a triangle having three sides S1, S2 and S3, in which side S1 is runs parallel to side 14A and side S2 runs parallel to side 14B. Sides S1, S2 and S3 can be conceptualized as vessel alignment lines or directions along which all, or at least a majority of, test vessels 27 are situated.

The above-described configuration increases the visibility of test vessels 27 while dissolution test apparatus 10 is operating in the front lowered position, especially the outermost situated test vessels 27, and further increases the accessibility of test vessels 27 when spindle head assembly 200 is located at its rear position for cleaning, alignment, removal and other purposes. While the remaining two test vessels 27 are illustrated as being situated in the inside region of vessel plate 25 away from sides 14A and 14B, these latter two test vessels 27 are often used as control vessels during dissolution procedures. Visibility of these latter two "inside" test vessels 27 is thus not as critical as visibility of the "outside" test vessels 27.

Figure 4:
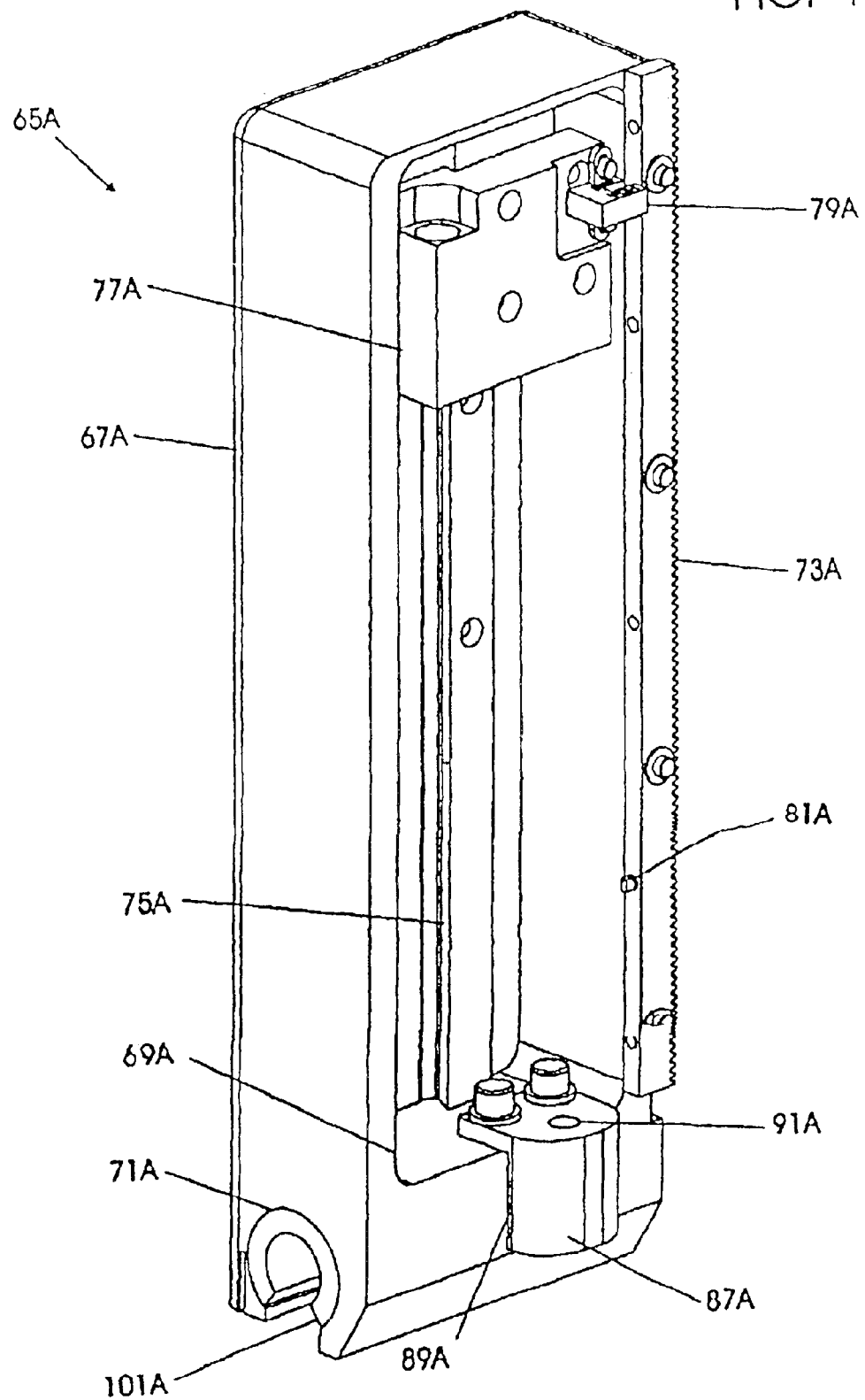
FIG. 4 is a perspective view of a movable support member provided with the dissolution test apparatus in accordance with the present invention.

Referring now to FIGS. 4–7, the details of spindle head transport assembly 60 are illustrated. FIG. 4 illustrates left lateral support member 65A. Left lateral support member 65A includes a body 67A having a cavity 69A adapted for facing spindle head assembly 200, and further includes a lower bore 71A formed at its lower end and a vertically-oriented, toothed rack gear 73A mounted along its rear side. A vertically-disposed slide track 75A is mounted to the innermost side of cavity 69A. A slide block 77A is movably connected to slide track 75A, and is adapted for attachment to spindle head assembly 200. In this manner spindle head assembly 200 slides between its front raised and front lowered positions along slide track 75A through the coupling provided by slide block 77A. A home flag sensor 79A, preferably of the optical type, is mounted to slide block 77A. Home flag sensor 79A interacts with a stop pin 81A (serving as the home flag) so that dissolution test apparatus 10 can determine when spindle head assembly 200 has reached the front lowered position. Stop pin 81A extends into cavity 69A from a surface of left lateral support member 65A that is located in the lower region of left lateral support member 65A.

A guide rod holder 87A is mounted at the lower end of left lateral support member 65A. In the exemplary embodiment, guide rod holder 87A is generally L-shaped to facilitate its mounting to left lateral support member 65A. Guide rod holder 87A includes a through-bore 91A for guiding a left guide rod 95A (see FIG. 7) associated with spindle head assembly 200. Left guide rod 95A is further described hereinbelow.

Figure 4A:
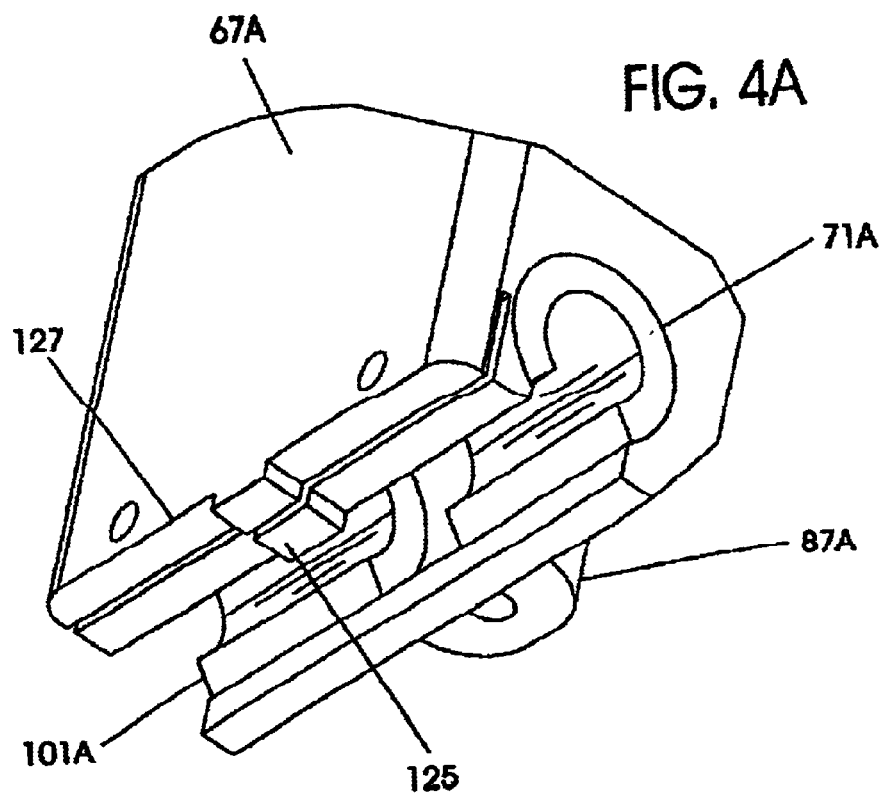
FIG. 4A is a detailed perspective view of a lower region of the support member illustrated in FIG. 4.

As best shown in FIG. 4A, one or more bushings 101A are inserted into lower bore 71A of left lateral support member 65A. Left lateral support member 65A is movably supported by left slide rail 105A (see FIGS. 1A, 2A, and 3A) by extending left slide rail 105A through lower bore 71A. As also shown in FIG. 4A, a protrusion 125 extends downwardly from a lower edge 127 of left lateral support member 65A. The function of protrusion 125 is described hereinbelow.

Figure 5A:
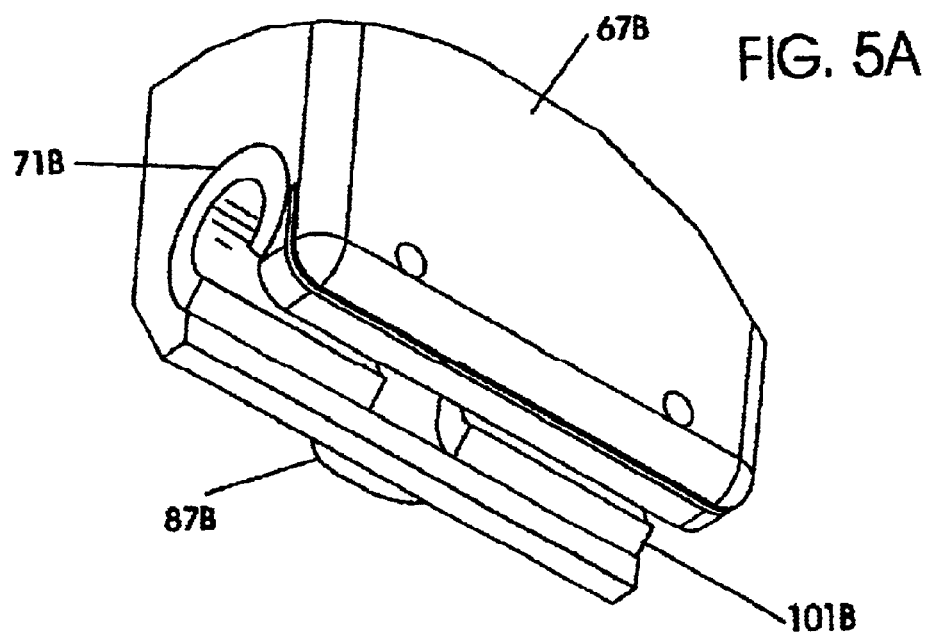
FIG. 5A is a detailed view of a lower region of the support member illustrated in FIG. 5.
Figure 5:
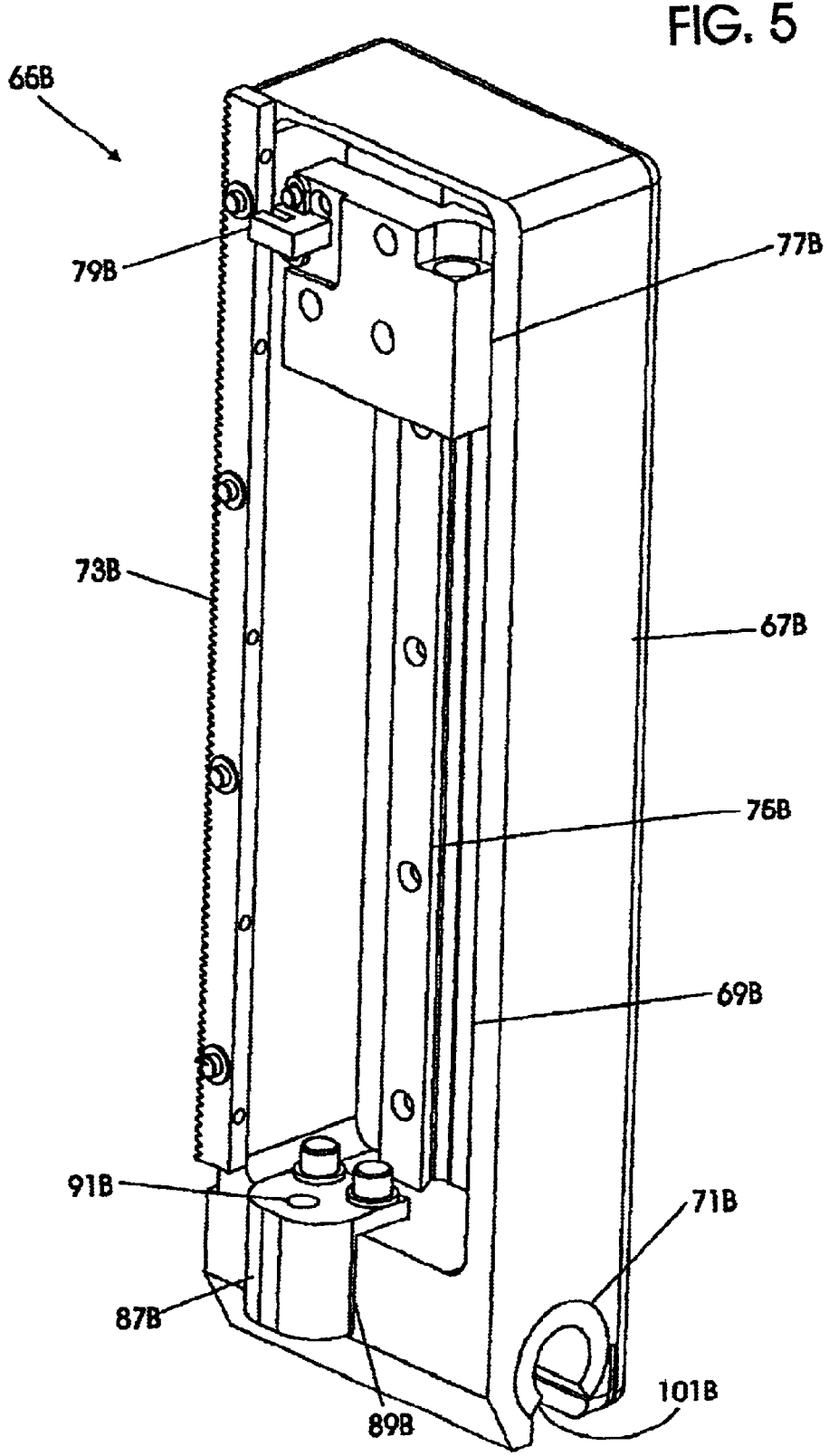
FIG. 5 is a perspective view of another movable support member provided with the dissolution test apparatus in accordance with the present invention.

FIGS. 5 and 5A illustrate right lateral support member 65B. Right lateral support member 65B includes many of the same components as left lateral support member 65A, which are similarly enumerated as follows: a body 67B having a cavity 69B adapted for facing spindle head assembly 200; a lower bore 71B; a vertically-oriented, toothed rack gear 73B; a vertically-disposed slide track 75B; a slide block 77B movably connected to slide track 75B; a home flag sensor 79B; a guide rod holder 87B with a through-bore 91B for guiding a right guide rod 95B (shown in FIGS. 1B and 2B); and one or more bushings 101B inserted into lower bore 71B of right lateral support member 65B, such that right lateral support member 65B is movably supported by right slide rail 105B (see FIGS. 1A, 2A, and 3A). Right lateral support member 65B, however, differs from left lateral support member 65A in at least two respects. First, a stop pin extends into cavity 69B from a surface of right lateral support member 65B that is located in the upper region of right lateral support member 65B, instead of in the lower region thereof. In FIG. 5, the stop pin for right lateral support member 65B is concealed by home flag sensor 79B and thus is not specifically shown. Home flag sensor 79B interacts with this stop pin (again serving as the home flag) at the upper location so that dissolution test apparatus 10 can determine when spindle head assembly 200 has reached the front raised position. The second difference is that a protrusion such as protrusion 125 in FIG. 4A is not necessary in the case of right lateral support member 65B.

Figure 6:
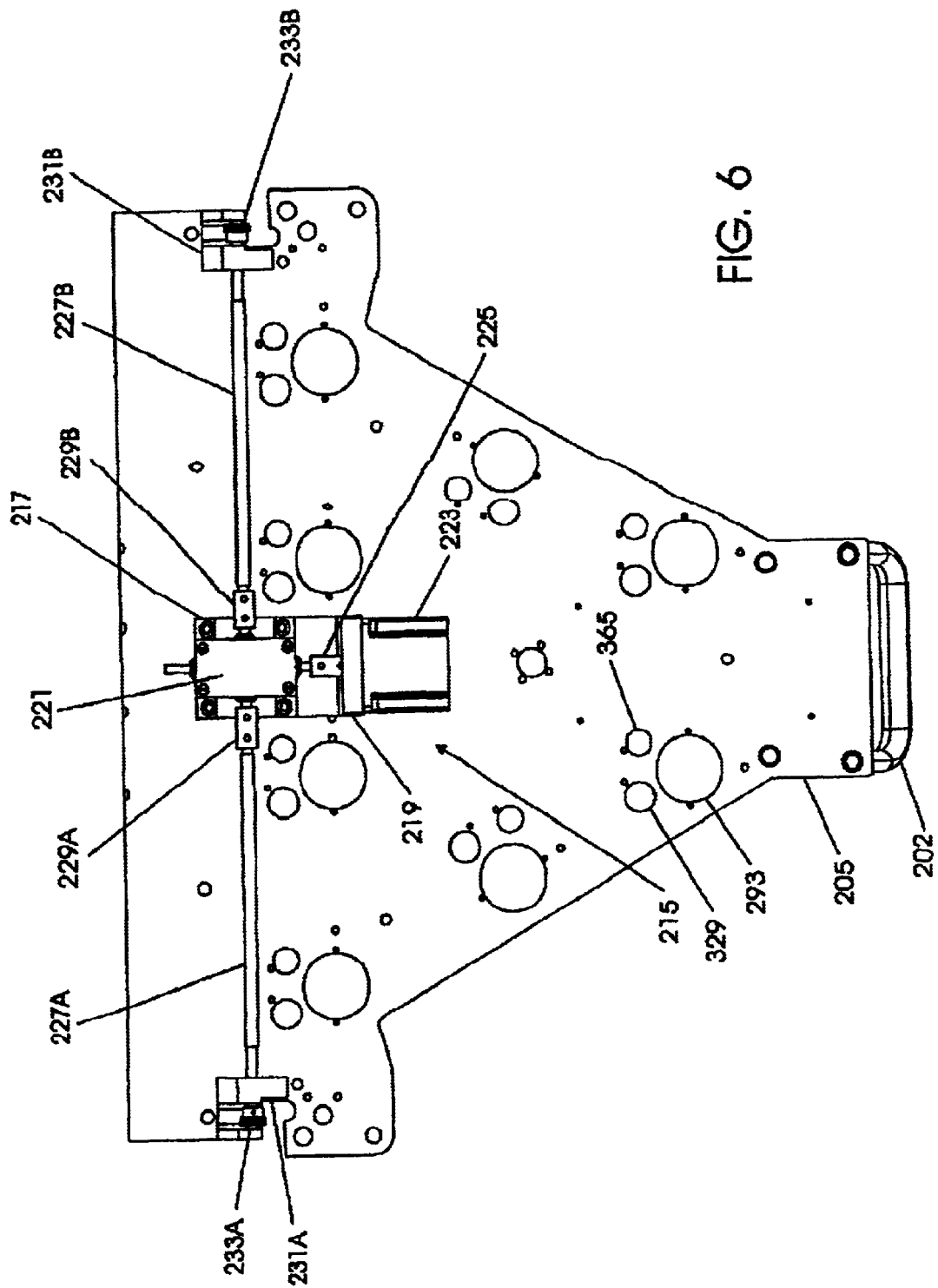
FIG. 6 is a top plan view of a base support member of a spindle head assembly provided with the dissolution test apparatus in accordance with the present invention, including a motorized lift assembly mounted on the base support member.
Figure 6A:
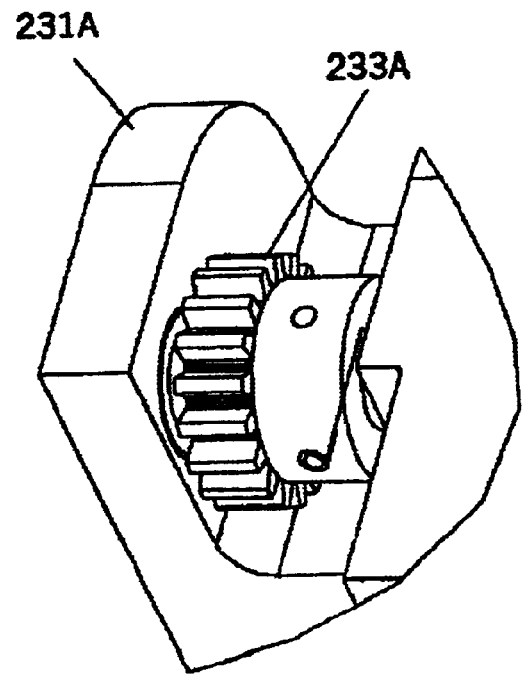
FIG. 6A is a detailed perspective view of a portion of the motorized lift assembly illustrated in FIG. 6.

Referring to FIGS. 6 and 6A, a base support plate 205 of spindle head assembly 200 is illustrated. A lift drive assembly, generally designated 215, is mounted on base support plate 205 and provides the power and connections needed to operatively couple spindle head assembly 200 to left and right lateral support members 65A and 65B, and accordingly to enable spindle head assembly 200 to be automatically driven between its front raised and front lowered positions. Lift drive assembly 215 includes a gearbox mounting plate 217 mounted to base support plate 205, and a lift motor mounting plate 219 mounted to gearbox mounting plate 217. A gearbox 221 is attached to gearbox mounting plate 217, and a lift motor 223 is likewise attached to lift motor mounting plate 219. The shaft of lift motor 223 is connected to gearbox 221 through a motor-to-gearbox coupling 225. Gearbox 221, using a worm gear drive or similar arrangement, translates the torque produced by lift motor 223 into transversely-oriented torque provided to drive shafts 227A and 227B disposed on each side of gearbox 221 and connected to gearbox 221 through gearbox shaft couplings 229A and 229B. The outer ends of drive shafts 227A and 227B are respectively supported in pillow blocks 231A and 231B mounted to base support plate 205. As best shown in FIG. 6A, toothed gears or pinions 233A and 233B are respectively supported on the outer ends of drive shafts 227A and 227B at each pillow block 231A and 231B. When spindle head assembly 200 is operatively connected to left and right lateral support members 65A and 65B, each pinion 233A and 233B meshes with its corresponding left or right vertical rack 73A or 73B (see FIGS. 4 and 5) to enable spindle head assembly 200 to be driven along left and right slide tracks 75A and 75B between its front raised and front lowered positions.

Figure 7A:
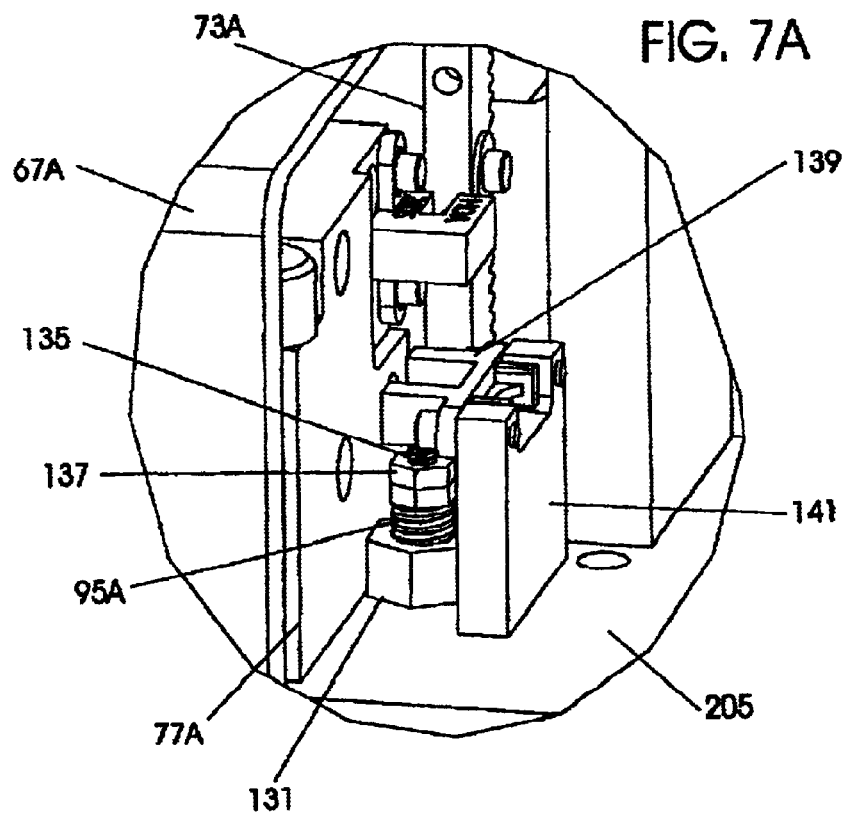
FIG. 7A is a detailed perspective view of the support member shown in FIG. 7, illustrating an upper section of a spindle head guide assembly equipped with a lift rod.
Figure 7B:
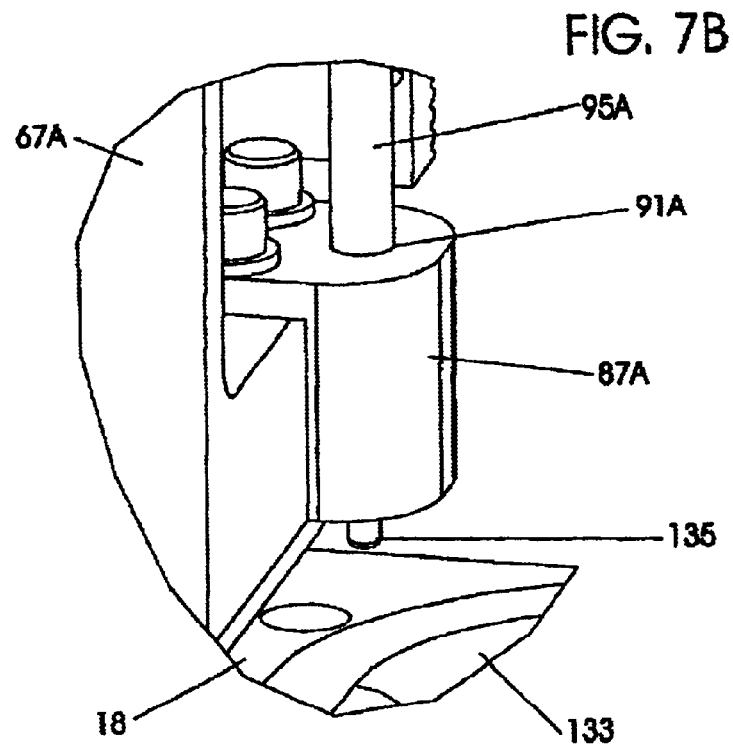
FIG. 7B is a detailed perspective view of the support member shown in FIG. 7, illustrating a lower section of the spindle head guide assembly equipped with a lift rod.

Referring now to FIGS. 7, 7A and 7B, the function of left guide rod 95A of spindle head assembly 200 is illustrated. As shown in FIG. 7, left guide rod 95A extends through a bore of base support plate 205 and through-bore 91A of guide rod holder 87A of left lateral support member 65A. Right guide rod 95B is analogously supported, but does not include the features of left guide rod 95A that will now be described. As best shown in FIG. 7A, left guide rod 95A is adjustably supported by base support plate 205 by threading a nut 131 onto a threaded upper portion of left guide rod 95A. Left guide rod 95A differs from right guide rod 95B in that a lift rod 135 is movably disposed within left guide rod 95A. Lift rod 135 is prevented from completely dropping out of left guide rod 95A by threading one or more nuts 137 onto a threaded portion of lift rod 135. A lift rod sensor 139 is operatively positioned in alignment with lift rod 135 with the assistance of a mounting block 141 attached to base support plate 205. As shown in FIG. 7B, the lowermost end of lift rod 135 protrudes beyond the bottom surface of guide rod holder 87A. When spindle head assembly 200 is in its proper rear position, lift rod 135 does not contact upper plate 18 of frame assembly 12.

Lift rod 135 serves as a home flag for lift rod sensor 139 to prevent damage to both dissolution test apparatus 10 and the operative components of spindle head assembly 200. Such damage might result from an operator erroneously attempting to lower spindle head assembly 200 while spindle head assembly 200 is in its rear position, instead of first transporting spindle head assembly 200 to the front raised position and then correctly causing spindle head assembly 200 to lower into the front lowered, operative position. Referring generally to FIG. 7B, it can be seen that if spindle head assembly 200 erroneously begins to lower toward upper plate 18 of frame assembly 12 from the rear position, left guide rod 95A (as well as right guide rod 95B) will move through bore 91A and 91B of guide rod holder 87A and 87B, and lift rod 135 will quickly come in contact with upper plate 18. As left guide rod 95A continues to move downwardly with spindle head assembly 200, further downward movement of lift rod 135 is arrested by upper plate 18. As a result, and referring generally to FIG. 7A, this further downward movement of spindle head assembly 200 causes lift rod 135 to break the sensing plane of lift rod sensor 139. When lift rod sensor 139 is tripped in this manner, electronic control circuitry provided on-board with dissolution test apparatus 10 causes spindle head assembly 200 to automatically reverse its direction and move back up to the proper rear position shown in FIGS. 1A and 1B, thereby preventing possibly severe damage to one or more components of dissolution test apparatus 10.

Referring back to FIG. 7, it can be envisioned that lift rod sensor 139 will not be tripped if spindle head assembly 200 is first correctly moved to the front raised position prior to attempting to move spindle head assembly 200 into the front lowered position. This is because dissolution test apparatus 10 includes a left alignment hole 144A through which left guide rod 95A (and thus lift rod 135) travels during movement of spindle head assembly 200 from the front raised position to the front lowered position. Dissolution test apparatus 10 likewise includes a right alignment hole 144B (see FIG. 1A) through which right guide rod 95B travels. Left and right guide rods 95A and 95B and their corresponding left and right alignment holes 144A and 144B cooperate to maintain spindle head assembly 200 in proper alignment with vessel plate 25 and each individual test vessel 27 as spindle head assembly 200 moves from the front raised position to the front lowered position. In the exemplary embodiment shown in FIG. 7, alignment hole 144A is formed in vessel plate 25. Accordingly, when spindle head assembly 200 travels from the front raised position to the front lowered position, lift rod 135 does not encounter any intervening structure to cause its upper end to break the plane of lift rod sensor 139. As shown in FIGS. 1–3, left and right guide rod tubes 146A and 146B are respectively disposed in register with their corresponding alignment holes 144A and 144B. Thus, each guide rod 95A and 95B (including lift rod 135 associated with left guide rod 95A) moves through its corresponding alignment hole 144A and 144B into guide rod tube 146A and 146B in order to prevent guide rods 95A and 95B from injuring an operator of dissolution test apparatus 10.

In order to further ensure proper alignment of the operative components of spindle head assembly 200 such as agitator shafts 274 with respect to the inside surface or surfaces of each test vessel 27, it is preferred that some form of vessel alignment means be provided for centering each test vessel 27 with respect to its mounting aperture in vessel plate 25 and/or its corresponding agitator shaft 274. The alignment means can take the form of a vessel alignment ring, for which novel embodiments are described in U.S. patent application Ser. No. 09/697,963, assigned to the assignee of the present invention, the entire disclosure of which is incorporated herein.

Figure 9A:
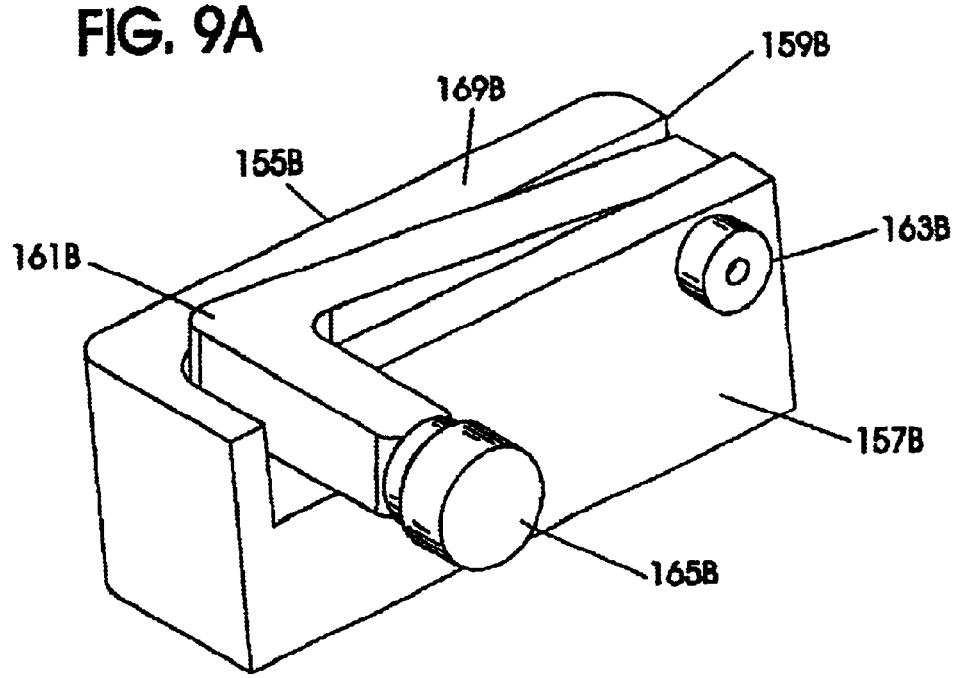
FIG. 9A is another latch assembly provided with the dissolution test apparatus in accordance with the present invention.
Figure 9B:
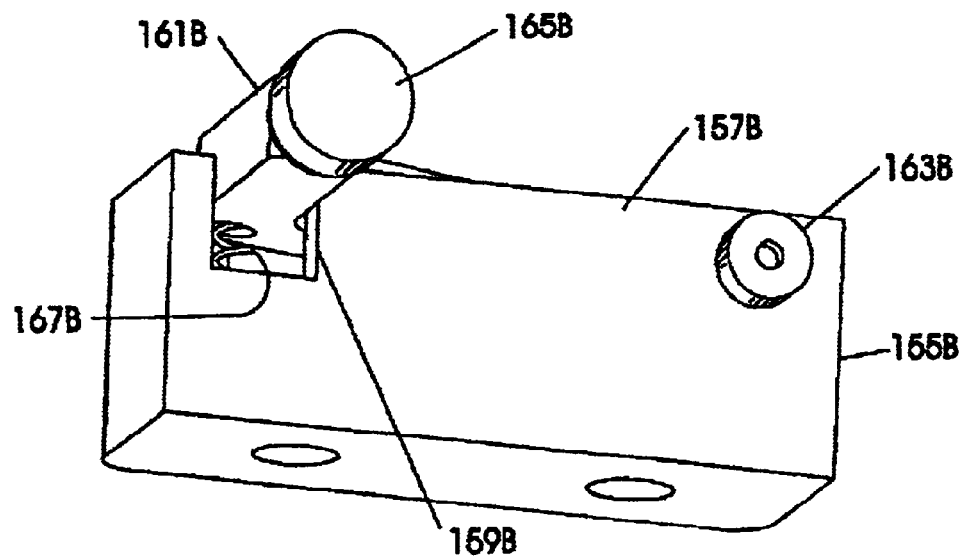
FIG. 9B is another perspective view of the latch assembly illustrated in FIG. 9A.

Referring to FIGS. 1B, 2B or 3B, front and rear latches 155A and 155B, respectively, are mounted in recesses on at least one side of upper plate 18 of frame assembly 12. Front latch 155A assists in locking spindle head assembly 200 in the front raised (and consequently front lowered) position, while rear latch 155B likewise assists in locking spindle head assembly 200 in the rear position. One preferred design of front latch 155A is illustrated in FIGS. 8A and 8B, and one preferred design of rear latch 155B is illustrated in FIGS. 9A and 9B. Referring first to FIGS. 8A and 8B, front latch 155A includes a latch block 157A having an upper recess 159A in which an L-shaped latch head 161A pivots about a pivot member 163A. Latch head 161A includes a handle 165A to facilitate its manipulation by an operator of dissolution test apparatus 10. As shown in FIG. 8B, a spring 167A urges latch head 161A upwardly away from recess 159A such that latch head 161A protrudes above a top surface 169A of latch block 157A. Latch head 161A interacts with protrusion 125 of left lateral support member 65A (see FIG. 4A). When spindle head assembly 200 moves with left and right lateral support members 65A and 65B fully into the front raised position from the rear position, latch head 161A engages protrusion 125 to lock spindle head assembly 200 into position. Prior to moving spindle head assembly 200 from the front raised position to the rear position, latch head 161A must be pushed downwardly against the biasing force of spring 167A to disengage latch head 161A from protrusion 125. As shown in FIGS. 9A and 9B, rear latch 155B has a structure similar to that of front latch 155A, and functions analogously to releasably lock spindle head assembly 200 into its rear position.

Figure 10:
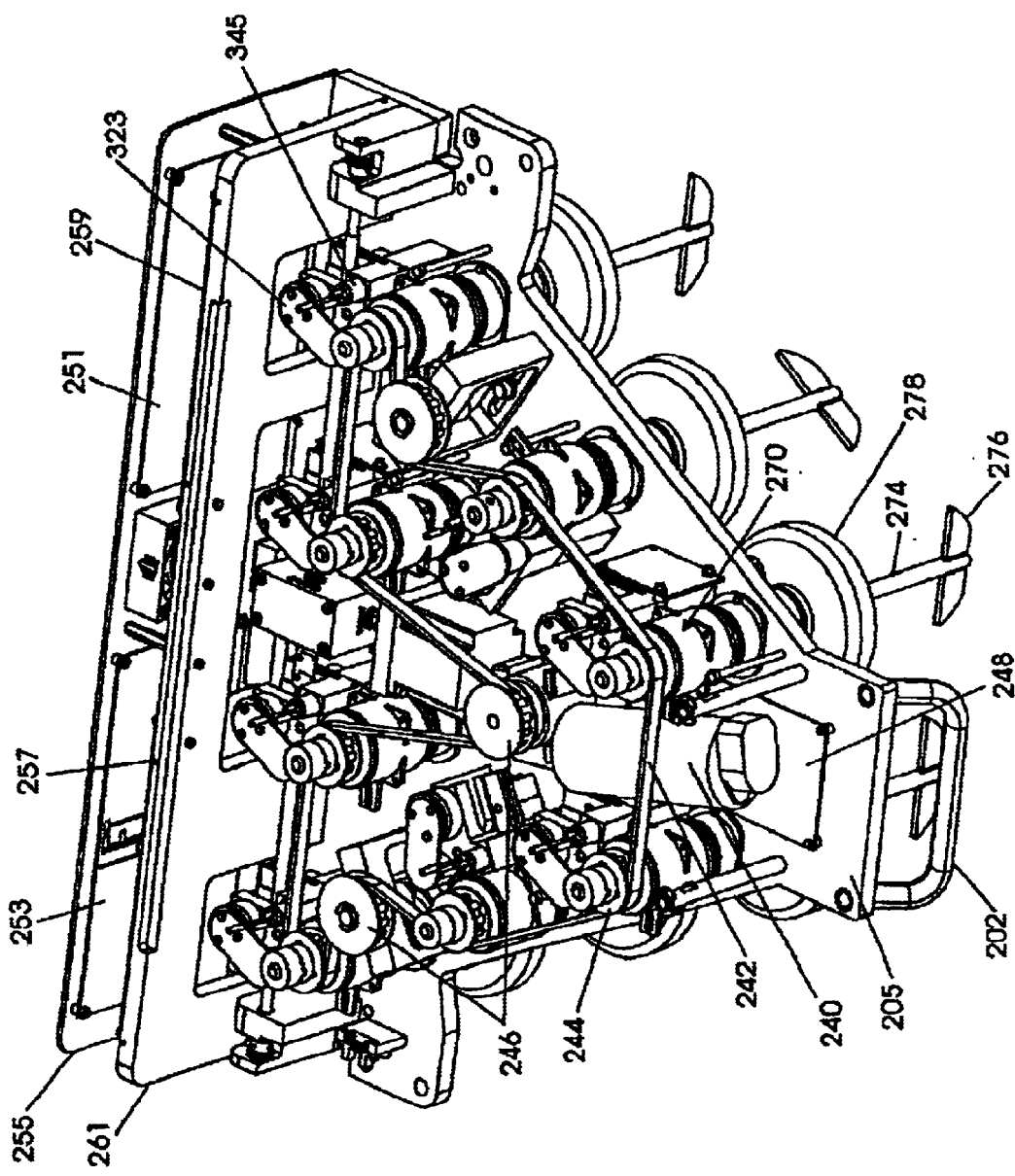
FIG. 10 is a perspective view of the spindle head assembly, with its top cover removed, as provided with the dissolution test apparatus in accordance with the present invention.

Referring now to FIG. 10, the arrangement of many of the operative components of spindle head assembly 200 is illustrated in detail, all of which are preferably directly or indirectly supported by base support plate 205. In association with each test vessel site, spindle head assembly 200 includes a spindle mechanism, generally designated 270, and a combined probe/dosage delivery mechanism, generally designated 310. A spindle drive motor 240 provides power to each spindle mechanism 270 through transmission means. Preferably, transmission means includes an endless belt 242 that operatively drives pulleys 244 of each spindle mechanism 270. A plurality of idler pulleys 246, some or all of which are adjustable, are provided to maintain proper tension of belt 242 throughout spindle head assembly 200. A printed circuit board (PCB) 248 contains electronics for controlling the operation of spindle drive motor 240. Spindle head assembly 200 also includes a main PCB 251 and a lift motor PCB 253 mounted to a back plate 255 of spindle head assembly 200, and a cannula master PCB 257 and a temperature probe PCB 259 mounted to a stiffening plate 261 of spindle head assembly 200.

Referring to FIG. 11, a removable cover 265 for spindle head assembly 200 is illustrated. Preferably, spindle head cover 265 is hinged to spindle head assembly 200 at a rear location so that spindle head cover 265 can be conveniently opened from the front to provide easy access into the confines of spindle head assembly 200.

Figure 12:
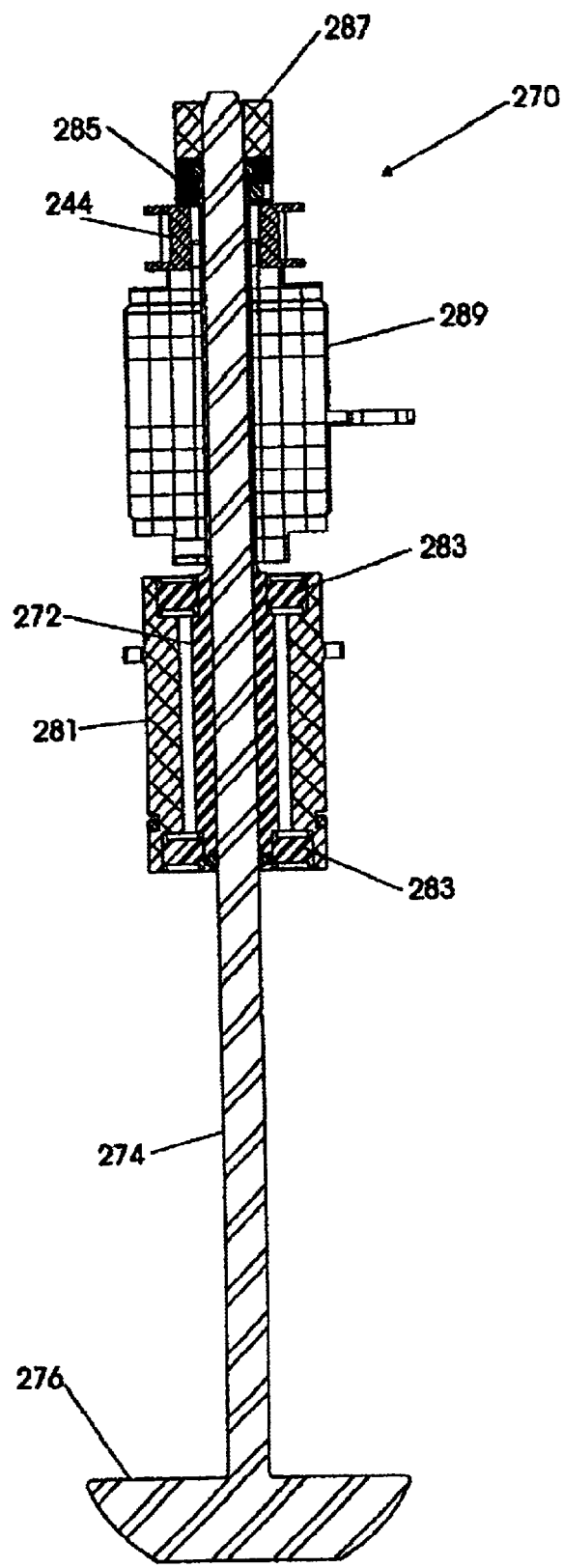
FIG. 12 is a cutaway, front elevation view of a spindle mechanism provided with the dissolution test apparatus in accordance with the present invention.

Referring to FIG. 12, the details of an exemplary spindle mechanism 270 are illustrated. A spindle 272 is press-fitted onto agitator shaft 274 and rotates within a spindle hub or bearing housing 281 with one or more bearings 283. As described hereinabove with reference to FIG. 10, pulley 244 is adapted to be operatively driven by spindle drive motor 240 of spindle head assembly 200 through the engagement of pulley 244 with belt 242. Pulley 244 is retained by a spindle collar 285, which contacts the upper portion of spindle 272. An agitator shaft collar 287 contacting agitator shaft 274 is disposed above spindle collar 285. Preferably, an electric or electromagnetic clutch/brake device 289 is operatively associated with spindle mechanism 270. Clutch/brake device 289 alternately engages and disengages spindle 272 to provide control over the operation of spindle mechanism 270. The brake portion prevents spindle 272 (and thus agitator shaft 274 and paddle 276) from rotating in an unintended manner when the clutch portion is disengaged from spindle 272. An operator of dissolution test apparatus 10 can thus program the sequence through which agitator shafts 274 operate in the media of test vessels 27, and can selectively start or stop one or more of spindle mechanisms 270 to facilitate manual procedures. Alternatively, a clutch device could be provided without the braking functionality, or no clutch provided at all. As shown in FIG. 11, for each test vessel location, spindle head cover 265 includes an aperture 291 to accommodate spindle mechanism 270. As shown in FIG. 6, base support plate 205 includes a similar aperture 293. Agitator shaft collars 287 can be seen disposed above spindle head cover 265 in FIGS. 1A, 2A and 3A.

Figure 13B:
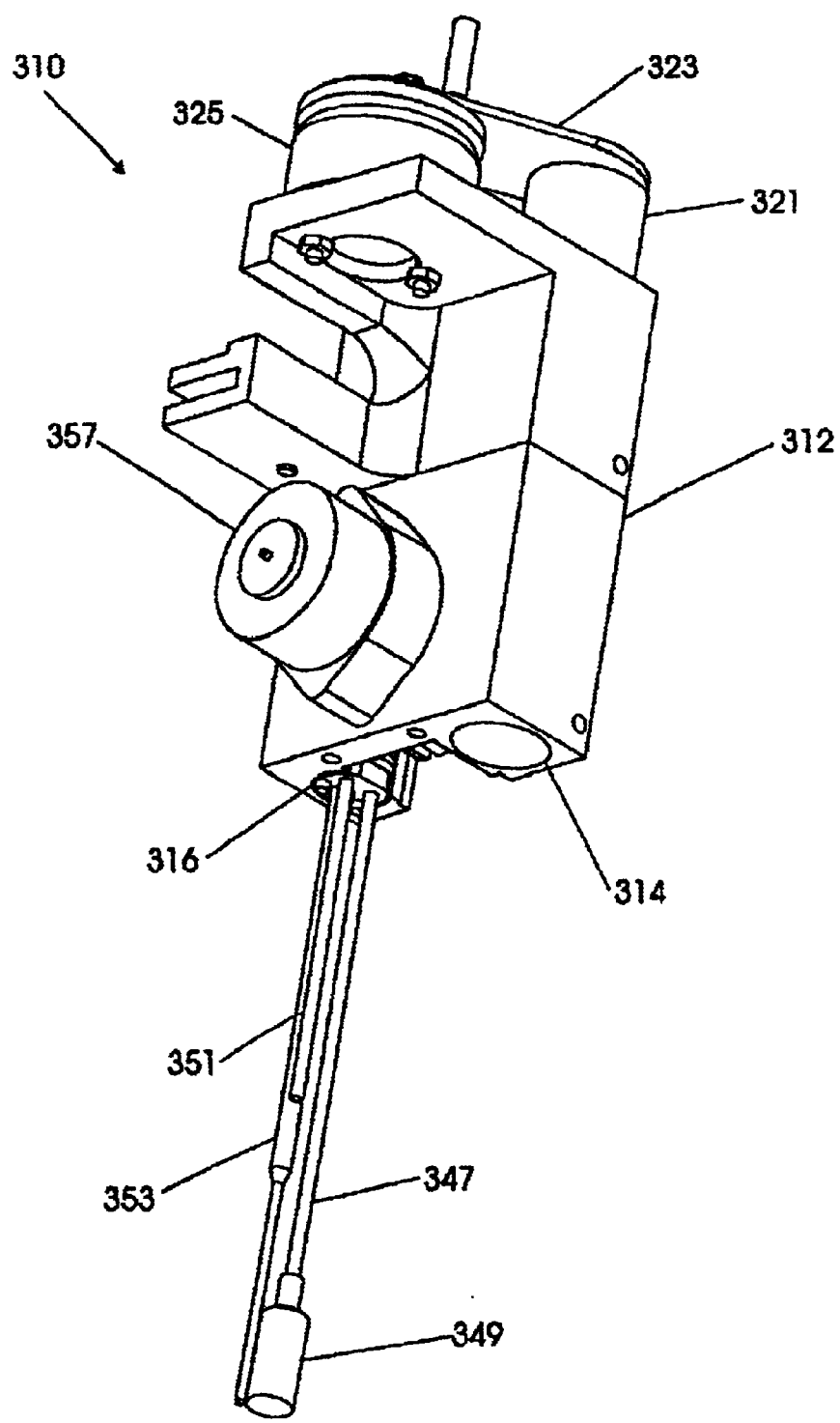
FIG. 13B is another perspective view of the combined probe/dosage delivery mechanism illustrated in FIG. 13A.

Referring to FIGS. 13A and 13B, the details of combined probe/dosage delivery mechanism 310 are illustrated. Combined probe/dosage delivery mechanism 310 integrates both a dosage delivery mechanism and a probe mechanism, and includes a main body 312 that defines both a dosage delivery passage 314 and a probe passage 316.

A dosage delivery tube 321, which could be constructed from either a clear material or an opaque material, is mounted in alignment with an inlet side of dosage delivery passage 314. A dosage retaining element such as a rotatable paddle or trap door 323 is operatively connected to a rotary actuator or solenoid 325, and alternately defines open and closed states of dosage delivery passage 314. The closed state is illustrated in FIGS. 13A and 13B, in which paddle 323 covers the open upper end of dosage delivery tube 321 and thereby prevents a dosage unit such as a tablet from dropping through dosage delivery passage 314 and into the media contained in a test vessel 27 situated below combined probe/dosage delivery mechanism 310. The open state is attained by energizing rotary actuator 325 to rotate paddle 323 out of the way of dosage delivery tube 321. As shown in FIG. 11, for each test vessel location, spindle head cover 265 includes a dosage unit inlet collar 327 in registry with an aperture (not specifically shown) to permit an operator to load a dosage unit into combined probe/dosage delivery mechanism 310. As shown in FIG. 6, base support plate 205 includes an aperture 329 to accommodate the delivery of dosage units into test vessels 27. Accordingly, dosage unit inlet collar 327, aperture 329 and dosage delivery passage 314 conjoin to define a dosage delivery path to each test vessel site.

In use, an operator of dissolution test apparatus 10 loads one or more dosage units through one or more dosage unit inlet collars 327 while each dosage delivery passage 314 is in the closed state. The lowermost dosage unit will come to rest on, and be supported by, each paddle 323 when situated in the closed state. At a predetermined times during operation of dissolution test apparatus 10, one or more paddles 323 will be rotated into the open state, thereby releasing a dosage unit into its corresponding test vessel 27. Rotary actuator 325 includes a spring-return element so that paddle 323 returns to the closed state once rotary actuator 325 is de-energized.

Referring again to FIGS. 13A and 13B, a probe holder 345 is movably disposed in probe passage 316. Probe holder 345 can be adapted to hold a variety of different types of probes. In the exemplary embodiment illustrated in FIGS. 13A and 13B, probe holder 345 holds a sample media withdrawal cannula 347 with a filter element 349, a sample media return cannula 351, and a temperature probe 353 such as the thermistor type. Main body 312 is adapted to support and provide a light shield for an optical encoder 355. Optical encoder 355 senses the vertical position of probe holder 345 with respect to main body 312 (for instance, the high point of probe holder 345), such as by sensing a change in distance provided by a notch (not shown) in probe holder 345. A stepper motor 357 is mounted to main body 312 to drive probe holder 345 vertically along the direction dictated by probe passage 316. Stepper motor 357 operatively engages a pinion gear 359 which meshes with a toothed rack 361 (see, e.g., FIG. 17) formed on probe holder 345. In accordance with instructions programmed into the control circuitry of dissolution test apparatus 10, probe holder 345 can be lowered into the media contained in its corresponding test vessel 27, measure temperature, draw a predetermined quantity of filtered sample from test vessel 27 (which is pumped to appropriate analytical equipment), return the unused portion of the sample back into test vessel 27, and then be retracted back out of the media until the next sampling or probing procedure. As shown in FIG. 11, for each test vessel location, spindle head cover 265 includes an aperture 363 to accommodate the probes and/or instruments held in probe holder 345, as well as their respective connections or fittings. As shown in FIG. 6, base support plate 205 includes a similar aperture 365.

Referring to FIG. 14, the underside of base support plate 205 of spindle head assembly 200 is illustrated with its operative components installed. It can be seen that each evaporation cover 278 includes apertures for accommodating the operation of agitator shaft 274, dosage delivery passage 314, and probe holder 345 and/or its individual probes or instruments.

Combined probe/dosage delivery mechanism 310 as illustrated in FIGS. 13A and 13B is preferred for its compactness and because it reduces complexity as well as the total number of operative modules associated with spindle head assembly 200. As an alternative, however, the probing and dosage delivery functions could be implemented in separate devices and mounted to spindle head assembly 200 in place of each combined probe/dosage delivery mechanism 310.

Figure 15:
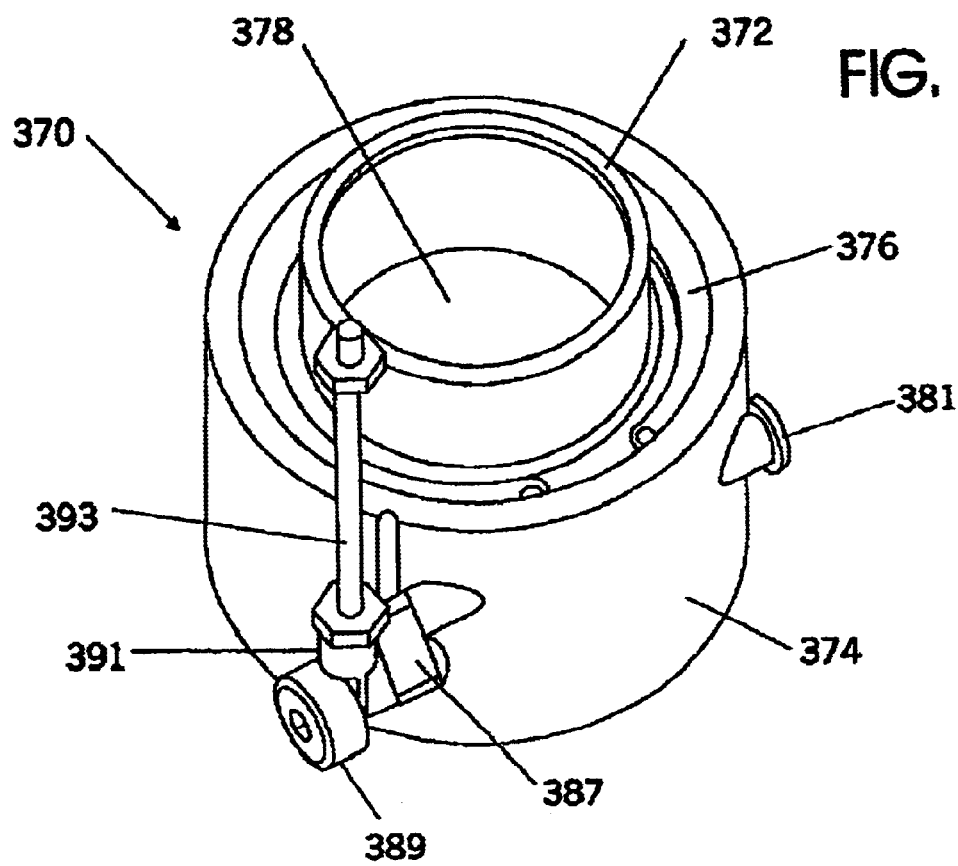
FIG. 15 is a perspective view of an alternative dosage delivery mechanism provided in accordance with the present invention.
Figure 16:
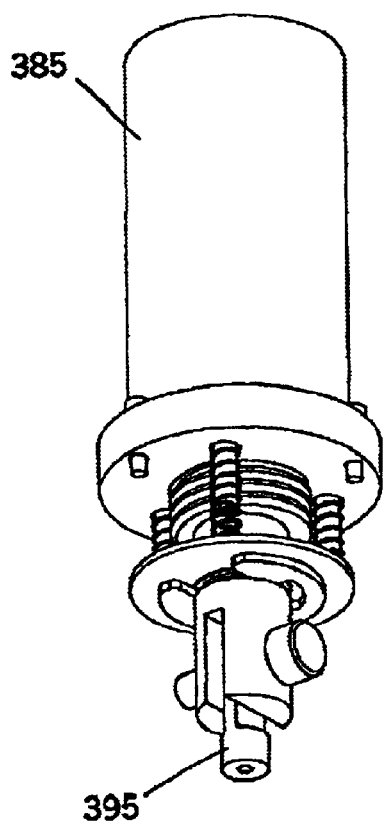
FIG. 16 is a perspective view of a linear actuator device operatively associated with the dosage delivery mechanism illustrated in FIG. 15.

Accordingly, referring to FIG. 15, a separate dosage delivery device is generally designated 370. Dosage delivery device 370 includes an upper dosage unit drop tube 372 secured to a lower dosage unit drop tube 374 by means of a snap ring 376 fitted into an annular groove formed on an inside surface of lower dosage unit drop tube 374. A rotatable paddle or trap door 378 is situated at the bottom end of upper dosage unit drop tube 372 and is operatively connected to a horizontally-oriented paddle shaft 381. Unlike paddle 323 of combined probe/dosage delivery mechanism 310 described previously, which rotates about an axis generally parallel with the dosage delivery path, paddle 378 of separate dosage delivery device 370 rotates about an axis generally transverse with the dosage delivery path. This latter axis is defined by paddle shaft 381. Also unlike paddle 323 of combined probe/dosage delivery mechanism 310, which is actuated by a rotary actuator 325, paddle 378 of separate dosage delivery device 370 is operatively connected through several linkage components to a linear actuator 385 such as the solenoid device shown in FIG. 16. Referring back to FIG. 15, the linkage components include a lever arm 387 interconnecting paddle shaft 381 with a pivoting member 389, and a yoke fitting 391 interconnecting pivoting member 389 with a linkage arm 393. Linkage arm 393 is adapted for connection with another yoke fitting 395, shown in FIG. 16, which in turn is operatively connected to the movable component of linear actuator 385.

Figure 17:
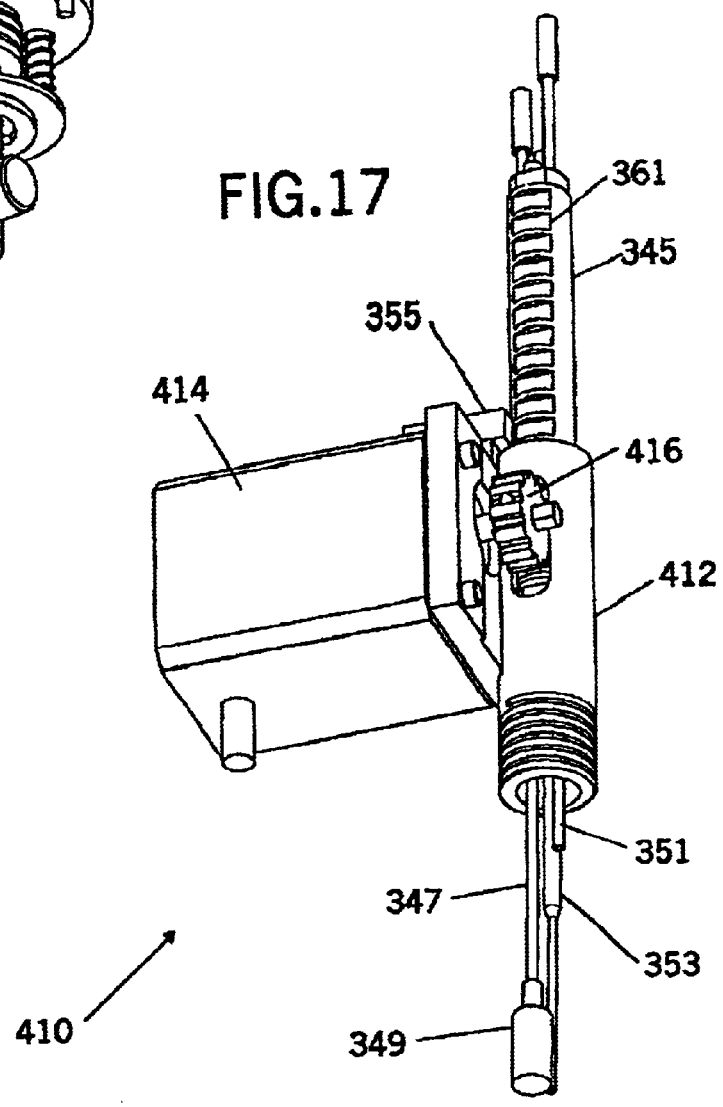
FIG. 17 is a perspective view of an alternative probe mechanism provided in accordance with the present invention.

Referring to FIG. 17, a separate probe device is generally designated 410. Probe holder 345 is movably disposed in a probe passage defined by a sleeve 412. As described previously, probe holder 345 can be adapted to hold a variety of different types of probes or instruments, such as liquid withdrawal cannula 347 with filter element 349, liquid dispensing cannula 351, and temperature probe 353, and its movement can be sensed by optical encoder 355. A stepper motor 414 drives the movement of probe holder 345 through a pinion gear 416 in meshing engagement with toothed rack 361 formed on probe holder 345.

Figure 18:
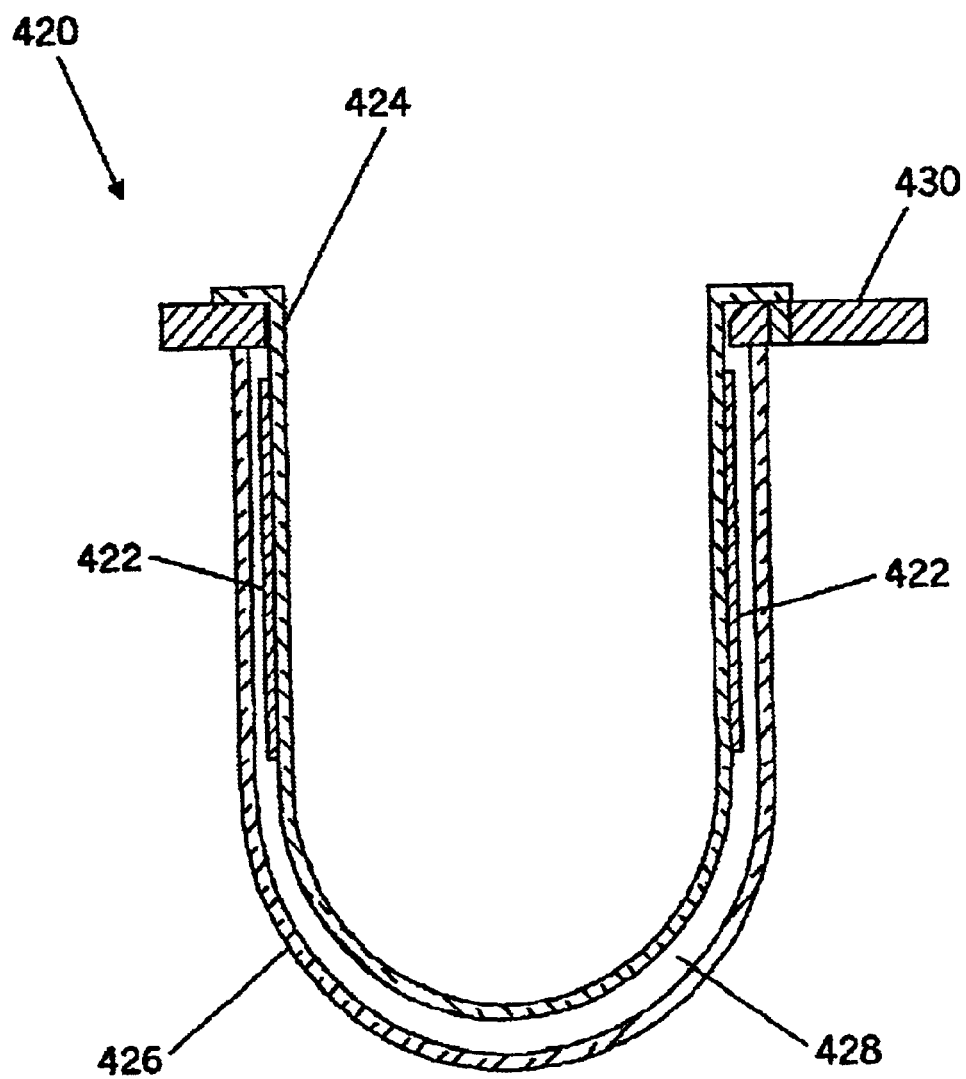
FIG. 18 is a cutaway, front elevation view of a modified test vessel provided with the present invention.

In an alternative embodiment according to the present invention, test vessels 27 are heated individually and directly by heater elements, instead of being heated collectively by submersion in a water bath. Accordingly, water bath container 23 and heater/pump unit 31 illustrated in FIGS. 1–3 can be eliminated and replaced with what may be termed direct or waterless vessel heating technology. Referring to the cross-sectional view of FIG. 18, a direct vessel heating system, generally designated 420, is illustrated. A heater element 422 is wrapped around the outer surface of a test vessel 424, and is adhered to test vessel 424 through the use of either a pressure-sensitive or heat-activated adhesive. Test vessel 424 is insulated from the ambient surroundings by inserting test vessel 424 into a vessel isolation jacket 426, which is preferably constructed from a clear material, so that a gap 428 is defined between test vessel 424 and vessel isolation jacket 428. A modified vessel plate 430 is provided to accommodate this configuration. Heater element 422 has a laminated structure that includes a plurality of thin films that are preferably constructed from a clear material. A heat conductive element such as one or more electrically resistive wires is embedded in one or more of the films, and supplies heat energy to the media contained in test vessel 424 to maintain temperature at a preset level. Additionally, a temperature-sensing element such as the RTD type can also be embedded in one or more of the films to control temperature. Moreover, an embedded protective sensor such as the thermistor type can be provided to prevent a runaway temperature event.

When direct vessel heating technology is utilized, heating system control circuitry, provided on-board with dissolution test apparatus 10 in communication with the main control circuitry, is employed to coordinate the respective operations of heater elements 422 (including its heat conductive element, temperature sensing element, and protective sensor) and temperature probe 353 of spindle head assembly 200 (see FIGS. 13A and 13B). The heating system control circuitry can simultaneously and independently operate and control heating-related functions at each test vessel 424 installed in dissolution test apparatus 10, with very good accuracy and in accordance with instructions programmed by an operator. For example, depending on the experimental procedures being implemented, each test vessel 424 can be maintained at a different set point temperature or can be subjected to a different variable temperature profile. Novel embodiments of the direct vessel heating technology are further described in U.S. patent application Ser. No. 09/603, 305, assigned to the assignee of the present invention, the entire disclosure of which is incorporated herein.

According to any of the embodiments described hereinabove, it can be seen that dissolution test apparatus 10 comprises a plurality of fully functional, individually controllable dissolution test systems. That is, each test vessel 27 effectively has its own dissolution test system. Moreover, spindle head assembly 200 contains all operative components of dissolution test apparatus 10 that are contemplated to require adjustment, manipulation, observation and/or replacement on a regular basis. These components are easily accessed by removing spindle head cover 265. Furthermore, these components are easily transported out of the way from test vessels 27 with minimal time and effort by moving spindle head assembly 200 from the front lowered position to the front raised position and to the rear position, so that test vessels 27 can be easily accessed. Finally, the tapered, triangular or trapezoidal shape of front section 14 of dissolution test apparatus 10 enables a high degree of visibility of test vessels 27 during their operation.

It will be understood that various details of the invention may be changed without departing from the scope of the invention. Furthermore, the foregoing description is for the purpose of illustration only, and not for the purpose of limitation—the invention being defined by the claims.

What is claimed is:

1. A dissolution test apparatus comprising:
    (a) a frame assembly for supporting a test vessel and including a front section and a rear section;
    (b) a transport assembly including first and second lateral support members, each of the first and second lateral support members including an upper section and a lower section, wherein each of the first and second lateral support members is movably mounted to the frame assembly and movable along a first axis to and from the front and rear sections of the frame assembly; and
    (c) a spindle head assembly comprising an operative component for interaction with the test vessel, the spindle head assembly movably connected to each of the first and second lateral support members, wherein the spindle head assembly is movable along a second axis to and from the upper and lower sections of the first and second lateral support members.

2. The apparatus according to claim 1 comprising a vessel plate mounted at the front section of the frame assembly, the vessel plate including a plurality of apertures defining vessel sites.

3. The apparatus according to claim 2 wherein the vessel plate includes first and second lateral edges defining a tapered width of the vessel plate, and the tapered width narrows in a direction from the rear section to the front section.

4. The apparatus according to claim 1 wherein the front section of the frame assembly includes first and second lateral edges defining a tapered width of the front section, and the tapered width narrows in a direction from the rear section to the front section.

5. The apparatus according to claim 1 comprising first and second lateral guide members mounted to the frame assembly and extending generally parallel to the first axis, wherein the transport assembly movably engages the first and second lateral guide members.

6. The apparatus according to claim 1 wherein the transport assembly comprises first and second vertical guide members extending generally parallel to the second axis, and the spindle head assembly is movably connected to the first and second vertical guide members.

7. The apparatus according to claim 2 wherein the apertures of the vessel plate are arranged in a generally triangular array.

8. The apparatus according to claim 3 wherein the apertures of the vessel plate are arranged in a generally triangular array between the first and second lateral edges of the vessel plate.

9. The apparatus according to claim 1 wherein the operative component comprises a shaft for insertion in the test vessel.

10. The apparatus according to claim 1 wherein the operable component comprises a probe mechanism.

11. The apparatus according to claim 1 wherein the operative component comprises a dosage delivery mechanism.

12. The apparatus according to claim 1 wherein the spindle head assembly comprises a spindle head cover movable for enabling access into the spindle head assembly.

13. The apparatus according to claim 11 wherein the dosage delivery mechanism comprises a dosage delivery passage, an actuator, and a dosage retaining element movable by the actuator between a closed state and an open state, and wherein at the closed state the dosage retaining element obstructs the dosage delivery passage, and at the open state the dosage retaining element is disposed in non-obstructive relation to the dosage delivery passage.

14. The apparatus according to claim 1 wherein the operative component comprises a combined probe/dosage delivery mechanism.

15. The apparatus according to claim 14 wherein the combined probe/dosage delivery mechanism comprises:
   (a) a body defining a dosage delivery passage;
   (b) a dosage retaining element movable between a closed state wherein the dosage retaining unit obstructs the dosage delivery passage and an open state wherein the dosage retaining unit is disposed in non-obstructive relation to the dosage delivery passage;
   (c) a probe member bore formed in the body; and
   (d) a probe member movably disposed in the probe member bore.

16. The apparatus according to claim 1 wherein:
   (a) the spindle head assembly is movable along the first axis between a rear position and an intermediate position, and is movable along the second axis between the intermediate position and an operative position;
   (b) at the rear position, the spindle head assembly is disposed above the rear section of the frame assembly in non-obstructive relation to the front section of the frame assembly;
   (c) at the intermediate position, the spindle head assembly is disposed above the front section of the frame assembly at a raised elevation; and
   (d) at the operative position, the spindle head assembly is disposed above the front section of the frame assembly at a lowered elevation for enabling the operative component to interact with the test vessel.

17. The apparatus according to claim 1 wherein the spindle head assembly comprises a plurality of vessel operation groups movable with the spindle head assembly, each vessel operation group including a shaft, a dosage delivery mechanism and a probe mechanism for interaction with the test vessel.

18. A dissolution test apparatus comprising:
   (a) a frame assembly for supporting a test vessel and including a front section and a rear section;
   (b) first and second lateral support members movably mounted to the frame assembly for movement between the front and rear sections along a first axis, each of the first and second lateral support members including an upper section and a lower section; and
   (c) a spindle head assembly comprising an operative component for interaction with the test vessel, the spindle bead assembly connected to the first and second lateral support members for movement therewith along the first axis, wherein the spindle head assembly is movable along a second axis to and from the upper and lower sections of the first and second lateral support members.

19. The apparatus according to claim 18 comprising an elongate spindle head guide member depending downwardly from the spindle head assembly toward the frame assembly.

20. The apparatus according to claim 18 comprising first and second lateral guide members mounted to the frame assembly and extending generally parallel to the first axis, wherein the first lateral support member movably engages the first lateral guide member and the second lateral support member movably engages the second lateral guide member.

21. The apparatus according to claim 18 comprising first and second vertical guide members respectively mounted to the first and second lateral support members and extending generally parallel to the second axis, wherein the spindle head assembly is movably connected to the first and second vertical guide members.

22. The apparatus according to claim 21 comprising first and second slide blocks respectively movably engaging the first and second vertical guide members, wherein the spindle head assembly is connected to the first and second slide blocks.

23. The apparatus according to claim 18 comprising a motorized lift assembly operatively coupling the spindle head assembly to the first and second lateral support members.

24. The apparatus according to claim 23 wherein the lift assembly comprises first and second gear members, the first and second lateral support members respectively comprise first and second gear meshing components, the first gear member operatively engages the first gear meshing component, and the second gear member operatively engages the second gear meshing component.

25. The apparatus according to claim 23 wherein the lift assembly is supported by the spindle head assembly.

26. The apparatus according to claim 18 wherein:
   (a) the spindle head assembly is movable along the first axis between a rear position and an intermediate position, and is movable along the second axis between the intermediate position and an operative position;
   (b) at the rear position, the spindle head assembly is disposed above the rear section of the frame assembly in non-obstructive relation to the front section of the frame assembly;
   (c) at the intermediate position, the spindle head assembly is disposed above the front section of the frame assembly at a raised elevation; and
   (d) at the operative position, the spindle head assembly is disposed above the front section of the frame assembly at a lowered elevation for enabling the operative component to interact with the test vessel.

27. The apparatus according to claim 26 wherein:
(a) the spindle head assembly comprises an elongate spindle head guide member having upper and lower ends and depending downwardly from the spindle head assembly, the upper end of the elongate spindle head guide member supported by the spindle head assembly;
(b) at the rear position, the lower end of the elongate spindle head guide member is spaced above the rear section of the frame assembly;
(c) at the intermediate position, the lower end of the elongate spindle head guide member is spaced above the front section of the frame assembly; and
(d) at the operative position, the lower end of the elongate spindle head guide member extends into the front section.

28. The apparatus according to claim 27 wherein the front section of the frame assembly includes an alignment bore and the elongate spindle head guide member extends into the alignment bore at the operative position of the spindle head assembly.

29. The apparatus according to claim 27 comprising:
(a) a lift rod movably disposed in the elongate spindle head guide member and including an upper end and a lower end; and
(b) a lift rod position sensor operatively aligned with the upper end of the lift rod and adapted to detect upward movement of the lift rod with respect to the elongate spindle head guide member.

30. The apparatus according to claim 19 comprising a lift rod movably disposed in the elongate spindle head guide member.

31. The apparatus according to claim 18 comprising a latch assembly mounted to the frame assembly and including a movable latch head releasably engaging the transport assembly into a locked position.

* * * * *